US011275019B2

(12) United States Patent
Ota et al.

(10) Patent No.: US 11,275,019 B2
(45) Date of Patent: Mar. 15, 2022

(54) LIQUID SAMPLE ANALYSIS METHOD AND LIQUID SAMPLE ANALYSIS DEVICE

(71) Applicant: ARKRAY, Inc., Kyoto (JP)

(72) Inventors: Shinichi Ota, Kyoto (JP); Shinya Nakajima, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 179 days.

(21) Appl. No.: 16/839,968

(22) Filed: Apr. 3, 2020

(65) Prior Publication Data

US 2020/0319088 A1 Oct. 8, 2020

(30) Foreign Application Priority Data

Apr. 8, 2019 (JP) .............................. JP2019-073450

(51) Int. Cl.
*G01N 33/48* (2006.01)
*G01N 21/05* (2006.01)
*G01N 1/14* (2006.01)
*G01N 33/49* (2006.01)
*G01N 33/493* (2006.01)

(52) U.S. Cl.
CPC .............. *G01N 21/05* (2013.01); *G01N 1/14* (2013.01); *G01N 33/493* (2013.01); *G01N 33/4915* (2013.01); *G01N 2001/1418* (2013.01)

(58) Field of Classification Search
CPC .... G01N 33/49; G01N 15/05; G01N 15/1434; A61B 5/14532; A61B 5/1455
USPC .......................................................... 356/39
See application file for complete search history.

(56) References Cited

U.S. PATENT DOCUMENTS

| 5,134,445 A | 7/1992 | Toge | |
|---|---|---|---|
| 2016/0377524 A1* | 12/2016 | Martin | ............... G01N 35/1097 73/864.81 |
| 2018/0372612 A1 | 12/2018 | Masuda | |

FOREIGN PATENT DOCUMENTS

| JP | 2018-112516 A | 7/2018 |
| JP | 2019-007893 A | 1/2019 |

OTHER PUBLICATIONS

The extended European search report issued by the European Patent Office dated Dec. 1, 2020, which corresponds to European Patent Application No. 20168467.7-1001 and is related to U.S. Appl. No. 16/839,968.

* cited by examiner

*Primary Examiner* — Md M Rahman
(74) *Attorney, Agent, or Firm* — Studebaker & Brackett PC

(57) ABSTRACT

A liquid sample analysis method including communicating a specific flow path with an aspirator via a branch flow path, aspirating air from the aspirator, aspirating a liquid sample into the sample supply path from the aspirator so that an entire amount of the aspirated air is accommodated in the branch flow path, communicating a sample extrusion path with a sample port, communicating a sheath fluid supply path with a sheath fluid port, and isolating the branch flow path from both the sample supply path and the specific flow path, extruding the liquid sample in the sample supply path so as to inflow into the sample flow path by causing a sheath fluid to inflow into the sheath fluid flow path from the sheath fluid supply path and causing the sheath fluid to inflow into the sample supply path from the sample extrusion path.

10 Claims, 24 Drawing Sheets

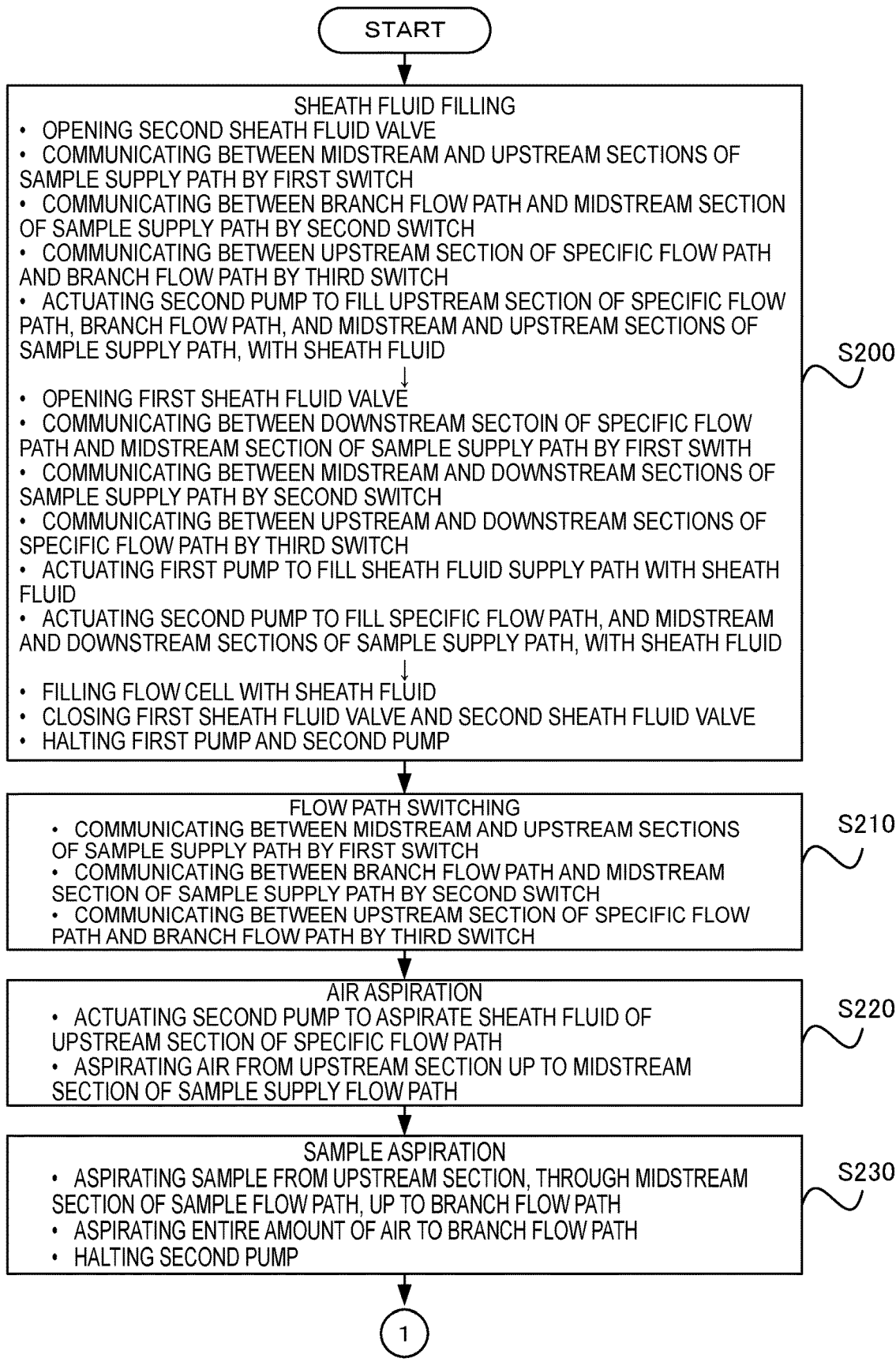

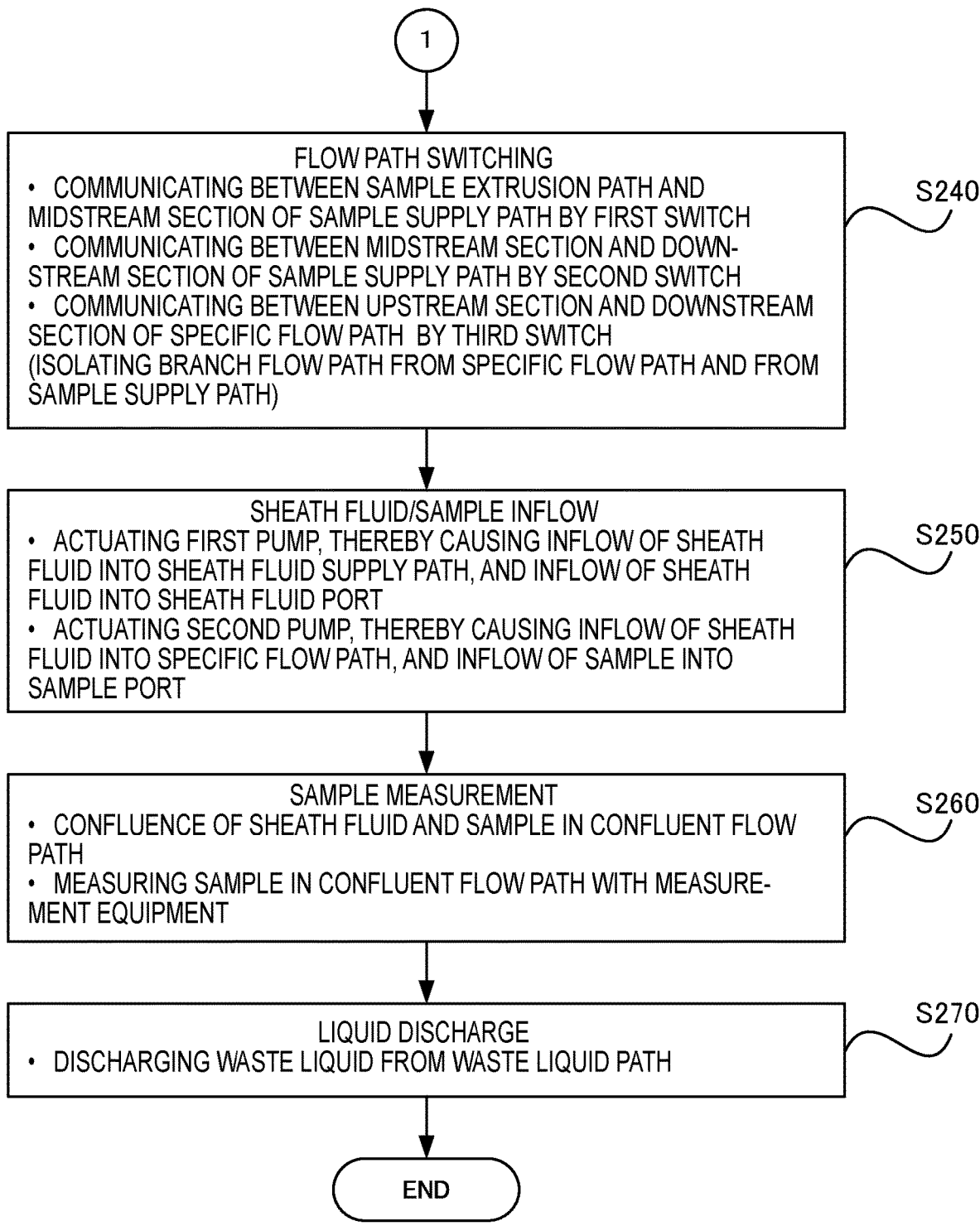

LIQUID SAMPLE ANALYSIS METHOD AND LIQUID SAMPLE ANALYSIS DEVICE

CROSS-REFERENCE TO RELATED APPLICATION

This application claims priority under 35 USC 119 from Japanese Patent Application No. 2019-073450, filed on Apr. 8, 2019, the disclosure of which is incorporated by reference herein.

BACKGROUND

Technical Field

The present disclosure relates to a liquid sample analysis method and a liquid sample analysis device that employ a flow cell.

Related Art

Japanese Patent Application Laid-Open (JP-A) Nos. 2018-112516 and 2019-7893 disclose flow cells that are equipped with two separated sheath fluid flow paths into which sheath fluid flowing from a sheath intake port, a sample flow path into which a liquid sample flows, and a confluent flow path where the two sheath fluid flow paths and the sample flow path join together and where imaging of formed elements contained in the liquid sample is performed.

An aspirator such as a nozzle to aspirate the liquid sample is provided at the leading end of a sample supply path for supplying the liquid sample into the flow cell configured as described above. Normally, prior to measuring a liquid sample, the sheath fluid filled a whole flow path from the flow path including the aspirator, through the flow cell, to a waste liquid path. If a liquid sample is directly aspirated in a state in which the aspirator is filled with the sheath fluid, then the liquid sample will be diluted by the sheath fluid before arriving at the flow cell, such that the formed elements are not able to be sufficiently observed in the confluent flow path of the flow cell.

SUMMARY

A liquid sample analysis method of the present disclosure includes communicating a specific flow path with an aspirator via a branch flow path, aspirating air from the aspirator, aspirating a liquid sample from the aspirator to the sample supply path so that an entire amount of the aspirated air is accommodated in a branch flow path, communicating a sample extrusion path with a sample port, communicating a sheath fluid supply path with a sheath fluid port, and isolating the branch flow path from both the sample supply path and the specific flow path, causing a sheath fluid to flow from the sheath fluid supply path to the sheath fluid flow path and causing the sheath fluid to flow from the sample extrusion path to the sample supply path so that the liquid sample in the sample supply path is extruded and is caused to flow into the sample flow path.

A liquid sample analysis device of the present disclosure includes: a specific pump controller that actuates a specific pump to aspirate air from the aspirator to a sample supply path, and further to aspirate a liquid sample from the aspirator to the sample supply path, and that halts the actuation of the specific pump in a state in which an entire amount of the aspirated air passes the second branch point and is accommodated in the branch flow path; a first switch controller that switches a first switch so that flow paths at a first branch point communicate from the sample extrusion path to a downstream side of the sample supply path, a second switch controller that switches a second switch so that flow paths at a second branch point communicate from an upstream side to the downstream side of the sample supply flow, and the third switch controller that switches the third switch so that the flow paths at the third branch point communicate the upstream side with the downstream side of the specific flow path; and a first pump controller that actuates a first pump to supply a sheath fluid into a sheath fluid supply path to cause the sheath fluid to flow into the sheath fluid flow path, and a second pump controller that actuates a second pump to supply the sheath fluid into a sample extrusion path so as to extrude the liquid sample in the sample supply path to cause the liquid sample to flow into the sample flow path.

An aspect of the present disclosure makes it possible to provide a liquid sample analysis method and a liquid sample analysis device, which make it possible to separate the sheath fluid from the liquid sample with air, to avoid dilution of the liquid sample with the sheath fluid, and, furthermore, to prevent the air, which separates the sheath fluid filling the aspirator in advance from the aspirated liquid sample, from flowing into the flow cell.

BRIEF DESCRIPTION OF THE DRAWINGS

Exemplary embodiments will be described in detail based on the following figures, wherein:

FIGS. 15A and 15B are flowcharts illustrating operation of an analysis device of the second exemplary embodiment of the present disclosure.

DETAILED DESCRIPTION

Figure 1:
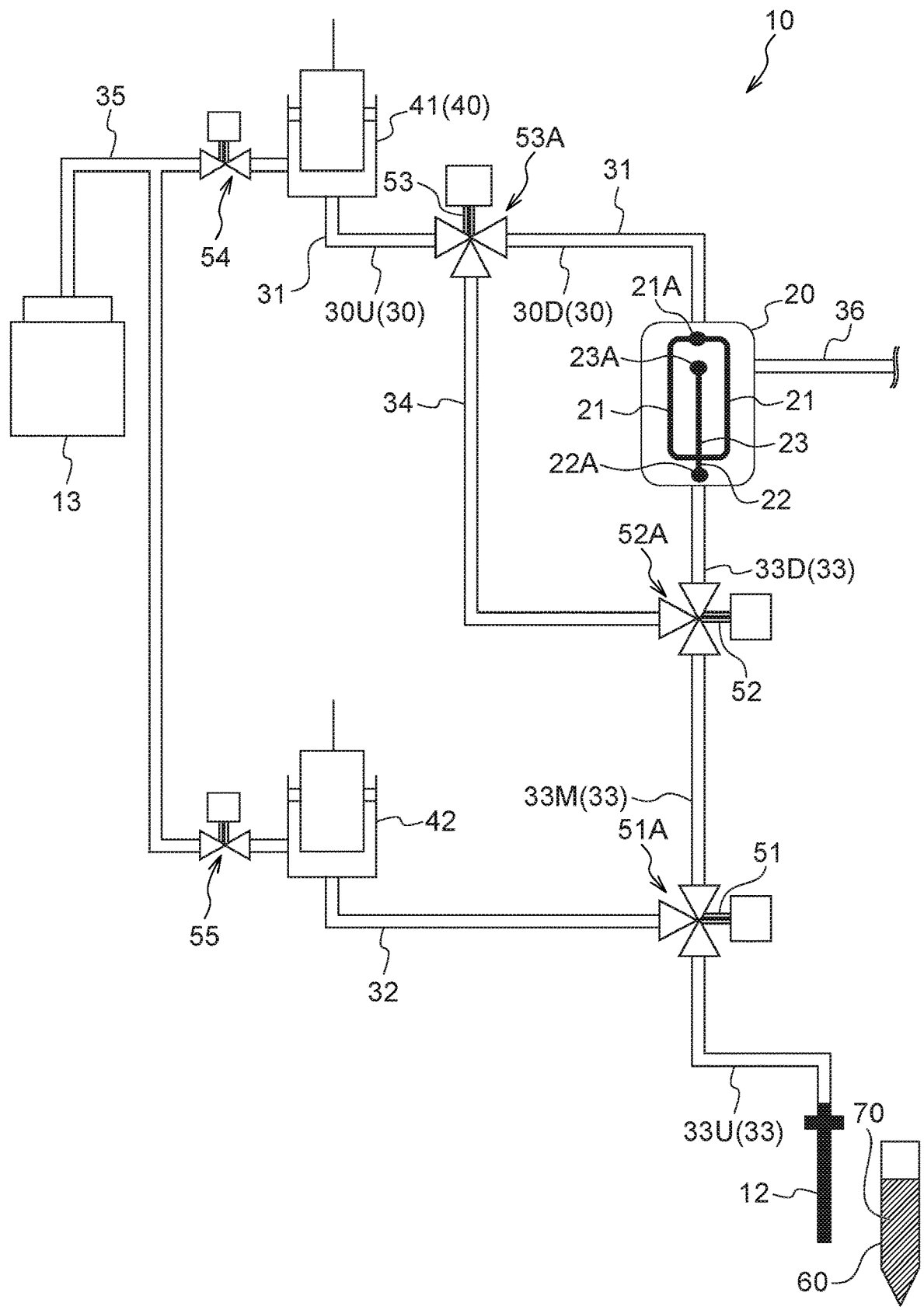
FIG. 1 is a schematic diagram of an analysis device of a first exemplary embodiment of the present disclosure.

An exemplary embodiment of the present disclosure is as described below. Note that reference numerals appended to each configuration element in the following description corresponds to reference numerals shown in the drawings for the convenience of reference. However, the present disclosure is obviously not limited thereby.

<Liquid Sample Analysis Method>

A liquid sample analysis method of the present disclosure employs the following configuration: a flow cell 20 including a sheath fluid flow path 21, a sample flow path 22, a confluent flow path 23 at which the sheath fluid flow path 21 and the sample flow path 22 join together, a sheath fluid port 21A that is at the upstream end of the sheath fluid flow path 21, and a sample port 22A that is at the upstream end of the sample flow path 22; a sheath fluid supply path 31 connected to the sheath fluid port 21A; an aspirator 12 to aspirate the liquid sample 70 and air 90; a sample supply path 33 that connects the aspirator 12 and the sample port 22A; a sample extrusion path 32 merging at a first branch point 51A provided on the sample supply path 33; a second branch point 52A provided on the sample supply path 33 between the first branch point 51A and the sample port 22A; a third branch point 53A provided either partway along the sheath fluid supply path 31 or partway along the sample extrusion path 32; a branch flow path 34 interconnecting the second branch point 52A and the third branch point 53A; and a first switch 51, a second switch 52, and a third switch 53 respectively provided at the first branch point 51A, the second branch point 52A, and the third branch point 53A to enable switching of respective three flow paths located at each of the first branch point, the second branch point and the third branch point.

The liquid sample analysis method of the present disclosure includes:

(1) switching the flow paths of the first switch 51, the second switch 52, and the third switch 53 so that a specific flow path 30, which is a flow path, among the sheath fluid supply path 31 and the sample extrusion path 32, that is provided with the third branch point 53A, communicates with the aspirator 12 via the branch flow path 34;
(2) aspirating the air 90 from the aspirator 12;
(3) aspirating the liquid sample 70 from the aspirator 12 to the sample supply path 33 so that an entire amount of the aspirated air 90 is accommodated in the branch flow path 34;
(4) switching the flow paths of the first switch 51, the second switch 52, and the third switch 53 so that the sample extrusion path 32 communicates with the sample port 22A, the sheath fluid supply path 31 communicates with the sheath fluid port 21A, and the branch flow path 34 is isolated from both the sample supply path 33 and the specific flow path 30;
(5) causing a sheath fluid 80 to flow from the sheath fluid supply path 31 to the sheath fluid flow path 21 and causing a sheath fluid 80 to flow from the sample extrusion path 32 to the sample supply path 33 so that the liquid sample 70 in the sample supply path 33 is extruded and is caused to flow into the sample flow path 22; and
(6) measuring, in the confluent flow path 23, the liquid sample 70 from the sample flow path 22 that is joined by the sheath fluid 80 from the sheath fluid flow path 21.

Note that, in the liquid sample analysis method of the present disclosure, it is preferable to aspirate a portion of the liquid sample 70 into the branch flow path 34 while aspirating the liquid sample 70.

Moreover, it is preferable that the liquid sample 70 is a liquid specimen derived from a biological body.

Furthermore, measuring the liquid sample 70 includes acquiring an image of the liquid sample 70.

<Liquid Sample Analysis Device>

The liquid sample analysis device 10 of the present disclosure is capable of executing the liquid sample analysis method described above, and includes a flow cell 20 including a sheath fluid flow path 21, a sample flow path 22, a confluent flow path 23 at which the sheath fluid flow path 21 and the sample flow path 22 join together, a sheath fluid port 21A that is an upstream end of the sheath fluid flow path 21, and a sample port 22A that is an upstream end of the sample flow path 22; a measurement device 11 installed at the confluent flow path 23; a sheath fluid supply path 31 connected to the sheath fluid port 21A; a first pump 41 provided on the sheath fluid supply path 31 and capable of supplying the sheath fluid 80 into the sheath fluid supply path 31; an aspirator 12 to aspirate the liquid sample 70 and the air 90; a sample supply path 33 that connects the aspirator 12 and the sample port 22A; a sample extrusion path 32 joining a first branch point 51A provided on the sample supply path 33; a second pump 42 provided on the sample extrusion path 32 and capable of supplying the sheath fluid 80 into the sample extrusion flow path 32; a sheath fluid storage unit 13 to supply the sheath fluid to the first pump 41 and the second pump 42; a second branch point 52A provided on the sample supply path 33 between the first branch point 51A and the sample port 22A; a third branch point 53A provided either partway along the sheath fluid supply path 31 or partway along the sample extrusion path 32; a branch flow path 34 interconnecting the second branch point 52A and the third branch point 53A; and a first switch 51, a second switch 52, and a third switch 53 respectively provided at the first branch point 51A, the second branch point 52A, and the third branch point 53A to enable switching of the respective three flow paths located at each of the first branch point 51A, the second branch point 52A and the third branch point 53A. In other words, the flow cell 20, a sample supply path 33, and an aspirator 12 in this order are connected each other.

The first switch 51, the second switch 52, and the third switch 53 may employ valves capable of opening and closing the respective three flow paths joining at each switch. For example, a configuration may be adopted in which a two-way valve is provided at each of the three flow paths, or a configuration may be adopted in which a single three-way valve is provided at the confluence of the three flow paths. A configuration in which a three-way valve is provided is preferable due to simplifying the flow path structure. The flow path switching can be achieved by combinations of opening and closing the valves on the three flow paths, communicating liquid or gas across a freely chosen two of the flow paths from out of the three flow paths, and setting the remaining flow path so as not to be in communication therewith.

The liquid sample analysis device 10 of the present disclosure further includes a controller 100 including a first pump controller 141 to control the first pump 41, a second pump controller 142 to control the second pump 42, a first switch controller 151 configured to control flow path switching in the first switch 51, a second switch controller 152 configured to control flow path switching in the second switch 52, a third switch controller 153 configured to control flow path switching in the third switch 53, and a measurement controller 111 configured to control measurement by the measurement device 11.

Either the sheath fluid supply path 31 or the sample extrusion path 32 on which the third branch point 53A is provided is referred to as the specific flow path 30. Either the first pump 41 or the second pump 42 that is provided on the specific flow path 30 is referred to as the specific pump 40. The specific pump 40 is configured so as to also be capable of aspirating the sheath fluid 80 from the specific flow path 30. Either the first pump controller 141 or the second pump controller 142 that controls the specific pump 40 is referred to as the specific pump controller 140. A side closer to the flow cell 20 in each of the specific flow path 30 and the sample supply path 33 is defined as a downstream side, and an opposite side thereto is defined as an upstream side. As described later, the specific pump 40 has a role of aspirating the liquid sample 70 and the air 90 from the aspirator 12 to the branch flow path 34.

In a state in which the sheath fluid supply path 31, the sample supply path 33, the sample extrusion path 32, and the branch flow path 34 are filled with the sheath fluid, the first switch controller 151 switches the first switch 51 so that the flow paths at the first branch point 51A communicate from the upstream side to the downstream side of the sample supply path 33. The second switch controller 152 switches the second switch 52 so that the flow paths at the second branch point 52A communicate from the upstream side of the sample supply path 33 to the branch flow path 34. The third switch controller 153 switches the third switch 53 so that the flow paths at the third branch point 53A communicate from the branch flow path 34 to the upstream side of the specific flow path 30.

Moreover, in the state in which the upstream side and the downstream side of the sample supply path 33 are in communication at the first branch point 51A, the upstream side of the sample supply path 33 and the branch flow path 34 are in communication at the second branch point 52A, and the branch flow path 34 and the upstream side of the specific flow path 30 are in communication at the third branch point 53A, the specific pump controller 140 actuates the specific pump 40 to aspirate the sheath fluid 80 from the specific flow path 30, thereby aspirating the air 90 from the aspirator 12 to the sample supply path 33 and furthermore aspirating the liquid sample 70 from the aspirator 12 to the sample supply path 33.

As described above, due to aspirating the air 90 before aspirating the liquid sample 70 from the aspirator 12 to the sample supply path 33, air is interposed between the sheath fluid 80 that has been filled in the aspirator 12, and the liquid sample 70. Thereby, the sheath fluid 80 and the liquid sample 70 are not in direct contact when the liquid sample 70 is aspirated from the aspirator 12 to the sample supply path 33. Accordingly, it is possible to avoid dilution of the liquid sample 70 with the sheath fluid 80 until the liquid sample 70 is introduced to the flow cell 20. The entire amount of the aspirated air 90 can be appropriately determined according to a shape and a cross-sectional area of the flow path from the aspirator 12 to the sample supply path 33, and a volume of the branch flow path 34.

Then, actuation of the specific pump 40 is halted in a state in which the entire amount of the aspirated air 90 passes the second branch point 52A and reaches the branch flow path 34. In other words, the aspirated air 90 is shunted from the sample supply path 33 to the branch flow path 34. The internal diameter and the length of the branch flow path 34 are determined so that the volume of the branch flow path 34 exceeds the volume of the air 90 aspirated from the aspirator 12. Thereby, the entire amount of the aspirated air 90 can be accommodated in the branch flow path 34.

Furthermore, in the state in which the entire amount of the aspirated air 90 reaches the branch flow path 34, the first switch controller 151 switches the first switch 51 so that the flow paths at the first branch point 51A communicate from the sample extrusion path 32 to the downstream side of the sample supply path 33, the second switch controller 152 switches the second switch 52 so that the flow paths at the second branch point 52A communicate from the upstream side to the downstream side of the sample supply path 33, and the third switch controller 153 switches the third switch 53 so that the flow paths at the third branch point 53A communicate the upstream side with the downstream side of the specific flow path 30.

An isolated state is thereby achieved in which the aspirated air 90 is sealed in the branch flow path 34, since the communication of liquid or gas between the branch flow path 34 containing the entire amount of the aspirated air 90 and both of the specific flow path 30 and the sample extrusion path 32 is interrupted.

Moreover, in the state in which the sample extrusion path 32 is in communication with the downstream side of the sample supply path 33 at the first branch point 51A, the upstream side of the sample supply path 33 is in communication with the downstream side thereof at the second branch point 52A, and the upstream side of the specific flow path 30 is in communication with the downstream side thereof at the third branch point 53A, the first pump controller 141 actuates the first pump 41 to supply the sheath fluid 80 into the sheath fluid supply path 31, and causes the sheath fluid 80 to flow into the sheath fluid flow path 21. In addition, the second pump controller 142 actuates the second pump 42 to supply the sheath fluid 80 into the sample extrusion path 32 so as to extrude the liquid sample 70 present in the sample supply path 33 to cause the liquid sample 70 to flow into the sample flow path 22.

The measurement controller 111 causes the measurement device 11 to measure the liquid sample 70 at the confluent flow path 23 where the liquid sample 70 from the sample flow path 22 is joined by the sheath fluid 80 from the sheath fluid flow path 21.

Note that the aspirated air 90 is sealed in the branch flow path 34 as described above. Therefore, even if the sheath fluid 80 flows in the sheath fluid supply path 31 and the sample extrusion path 32, effects of pressure or the like of the fluid delivery do not affect the branch flow path 34. Thereby, it is possible to prevent the air is sealed in the branch flow path 34 from flowing from the branch flow path 34 into the flow cell 20.

Note that portions of the aspirated liquid sample 70 in close proximity to the air 90 are sometimes diluted by sheath fluid 80 remaining in the flow path, and sometimes contain dirt from the flow path. Thus, it is preferable for the specific pump controller 140 to actuate the specific pump 40 to aspirate the sheath fluid 80 from the specific flow path 30 until a portion of the liquid sample 70 reaches the branch flow path 34. Thus, to ensure that a portion of liquid sample 70 is also sealed in the branch flow path 34 through the second switch 52, makes it possible to prevent a diluted liquid sample or a liquid sample containing dirt from flowing into the flow cell 20.

Note that with respect to the liquid sample 70, there are no particular limitations as long as the liquid sample 70 is a liquid capable of flowing in the flow cell 20. For example, the liquid sample 70 may be a liquid, or the liquid sample 70 may be diluted liquid produced by, for example, suspending, dispersing, or dissolving a solid in a liquid medium. When the liquid sample 70 is a liquid, for example, the neat liquid may be used as-is as the liquid sample 70, or a diluted liquid may be employed for the liquid sample 70 in which the neat liquid is suspended, dispersed, or dissolved in a liquid medium. There are no particular limitations to the liquid medium as long as the medium is capable of suspending, dispersing, or dissolving a solid, and examples of the medium include water, a buffer solution, or the like. The liquid sample 70 is preferably a liquid specimen derived from a biological body. The liquid specimen derived from a biological body is not particularly limited and examples thereof include urine, blood, saliva, sweat, and the like. The blood sample may, for example, be erythrocytes, whole blood, serum, blood plasma, or the like. Examples of the biological body include a human, a non-human animal, a plant, or the like, and the non-human animal may, for example, be a mammal other than a human, a reptile/amphibian, a fish, an insect, or the like. The liquid sample analysis method of the present disclosure is particularly appropriate to analysis of a liquid specimen derived from a biological body, for example human urine, as the liquid sample 70, and in particular to the analysis of formed elements contained therein.

The measurement device 11 may be appropriately selected according to the type of liquid sample 70 and measurement item, such as the component, physical property etc. of the liquid sample. The measurement device 11 may be photometric device such as a spectrophotometer, imaging device (for example a camera), or the like, and may be an electrometric device such as a sensor or the like. Due to being able to avoid the inflow of the air 90 into the flow cell 20 by employing the configuration described in the present disclosure, occurrence of bubbles inside the flow cell 20 can also be avoided. The configuration described in the present disclosure is accordingly advantageous in cases in which measurements by the measurement device 11 employed would be impeded by the presence of bubbles. For example, in cases in which an imaging device is employed as the measurement device 11 to observe and measure solid components suspended or dispersed in the liquid sample 70 using images obtained with the imaging device, the outline and shape of bubbles are imaged similarly to the solid components subject to measurement. There is accordingly a need to discriminate between solid components subject to measurement, and bubbles, and this impedes measurement. The present disclosure is accordingly particularly advantageously employed in cases in which an imaging device is employed as the measurement device 11.

Note that measurements referred to here include detecting a particular component of the liquid sample 70 in a quantitative or qualitative manner, acquiring images with an imaging device such as a camera and observing and analyzing such images.

Explanation follows regarding an exemplary embodiment of the present disclosure, with reference to the drawings.

First Exemplary Embodiment

FIG. 1 schematically illustrates a first exemplary embodiment of the analysis device 10, using urine as the liquid sample 70 and analyzing formed elements in the urine. In the present exemplary embodiment the sheath fluid supply path 31 and the sample supply path 33 are connected as flow paths to flow into the flow cell 20. A waste liquid path 36 is also connected as a flow path to flow out from the flow cell 20. For convenience the first exemplary embodiment will be described for a case in which the analysis device 10 is employed to analyze formed elements in urine, however the liquid sample 70 of the first exemplary embodiment is not limited to urine.

Configuration of Analysis Device 10

The flow cell 20 is preferably formed from a transparent material, for example, a material having a transparency to visible light of not less than 90%, such as, for example, glass, or a synthetic resin such as polymethyl methacrylate resin, a cyclo olefin polymer resin, a polydimethylsiloxane resin, a polypropylene resin, or the like. The flow cell 20 can be formed from such a material by sticking two rectangular shaped plate members thereof together. More specifically, the sheath fluid flow path 21 is formed as a rectangular shaped groove in the surface of one of such plate members, and a straight line shaped groove is also formed orthogonal to one of the short sides of the rectangular shape. The straight line shaped groove forms the sample flow path 22 extending outward from the short side, and forms the confluent flow path 23 extending inward from the short side. The sample flow path 22 has a leading end destination in the vicinity of the short side of the plate member. The confluent flow path 23 has a leading end destination in the vicinity of the short side of the sheath fluid flow path 21 on the opposite side thereto. The sheath fluid port 21A, the sample port 22A, and an waste liquid port 23A are formed as three holes in the other plate member. The sheath fluid port 21A is aligned with a position at a midpoint of the short side of the sheath fluid flow path 21 that does not orthogonally intersect the sample flow path 22 and confluent flow path 23. The sample port 22A is aligned with a position at the leading end of the sample flow path 22, and the waste liquid port 23A is aligned with a position at the leading end of the confluent flow path 23. Thus sticking the two plate members together forms the flow cell 20 which incorporates the sheath fluid port 21A that communicates the sheath fluid flow path 21 with outside, the sample port 22A that communicates the sample flow path 22 with outside, and the waste liquid port 23A that communicates the confluent flow path 23 with outside. The sheath fluid supply path 31 is connected to the sheath fluid port 21A. The sample supply path 33 is connected to the sample port 22A. The waste liquid path 36 is connected to the waste liquid port 23A.

In other words, the sheath fluid supply path 31 branches via the sheath fluid port 21A into two sheath fluid flow paths 21 inside the flow cell 20. On the other hand, the sample supply path 33 extends via the sample port 22A into the sample flow path 22 in the flow cell. Then, the two sheath fluid flow paths 21 and the sample flow path 22 join together to be the confluent flow path 23, which in turn extends via the waste liquid port 23A into the waste liquid path 36.

The aspirator 12 is formed as a nozzle with a leading end fitted to the most upstream end of the sample supply path 33. The aspirator 12 is a configuration element to aspirate the liquid sample 70 from a sample container 60 containing the liquid sample 70 using the first pump 41 serving as the specific pump 40, as described later. The first branch point 51A is set partway along the sample supply path 33, at which the first switch 51 configured by a three-way valve is provided. The sample extrusion path 32 is connected to the sample supply path 33 via the first switch 51. In other words, the sample extrusion path 32 joins the sample supply path 33 at the first branch point 51A.

The sheath fluid 80 (see FIG. 6 to FIG. 12) is supplied from the first pump 41 into the sheath fluid supply path 31. Moreover, the sheath fluid 80 is also supplied from the second pump 42 into the sample extrusion path 32. In the present exemplary embodiment, plunger pumps are employed for both the first pump 41 and the second pump 42, enabling the sheath fluid 80 to also be aspirated from the sheath fluid supply path 31 and the sample extrusion path 32. Note that although the first pump 41 functions as the specific pump 40 in the present exemplary embodiment as described later, the second pump 42 not serving as the specific pump 40 may employ a pump, such as a tube pump, that only has a fluid delivery function and does not have an aspiration function.

The sheath fluid storage unit 13 is a tank to store the sheath fluid 80 for supply to the flow cell 20 through the first pump 41 and the second pump 42. A sheath fluid transport path 35 extends from the sheath fluid storage unit 13 as tubing connected to the first pump 41 and the second pump 42. A first sheath fluid valve 54 is provided to the sheath fluid transport path 35 between the sheath fluid storage unit 13 and the first pump 41, and a second sheath fluid valve 55 is provided to the sheath fluid transport path 35 between the sheath fluid storage unit 13 and the second pump 42. The first sheath fluid valve 54 and the second sheath fluid valve 55 are both capable of opening and closing along only one direction.

Note that in the present exemplary embodiment, a side closer to the flow cell 20 in each of the sheath fluid supply path 31, the sample extrusion path 32, and the sample supply path 33 is defined as a downstream side, and an opposite side thereto is defined as an upstream side.

The second branch point 52A is also set on the sample supply path 33 between the first branch point 51A and the sample port 22A of the flow cell 20 (in other words at the downstream side of the first branch point 51A), at which the second switch 52 configured by a three-way valve is provided. On the other hand, the third branch point 53A is set partway along the sheath fluid supply path 31 (in other words between the first pump 41 and the sheath fluid port 21A of the flow cell 20), at which the third switch 53 configured by a three-way valve is provided. Further, the second branch point 52A and the third branch point 53A are interconnected through the branch flow path 34.

Note that the sheath fluid supply path 31 on which the third branch point 53A is provided is also referred to as the specific flow path 30. The first pump 41 to supply the sheath fluid 80 to the sheath fluid supply path 31 serving as the specific flow path 30 is also referred to as the specific pump 40.

The sheath fluid supply path 31, the sample extrusion path 32, the sample supply path 33, and the branch flow path 34, as well as the sheath fluid transport path 35 and the waste liquid path 36, are all configured by flexible and soft tubing (for example, TEFLON (registered trademark) tube).

The sample supply path 33 is divided into three parts by the first branch point 51A and the second branch point 52A, and the part of upstream side from the first branch point 51A is referred to as an upstream section 33U, the part between the first branch point 51A and the second branch point 52A is referred to as a midstream section 33M, and the part between the second branch point 52A and the sample port 22A is referred to as a downstream section 33D. In other words, the upstream section 33U and the midstream section 33M of the sample supply path 33 and the sample extrusion path 32 join together at the first branch point 51A. Moreover, the midstream section 33M and the downstream section 33D of the sample supply path 33 and the branch flow path 34 join together at the second branch point 52A.

Furthermore, the sheath fluid supply path 31 serving as the specific flow path 30 is divided into two parts by the third branch point 53A, and the part of the upstream side from the third branch point 53A is referred to as an upstream section 30U, and the part of the downstream side from the third branch point 53A is referred to as a downstream section 30D. In other words, the upstream section 30U and the downstream section 30D of the specific flow path 30 and the branch flow path 34 join together at the third branch point 53A.

Figure 2:
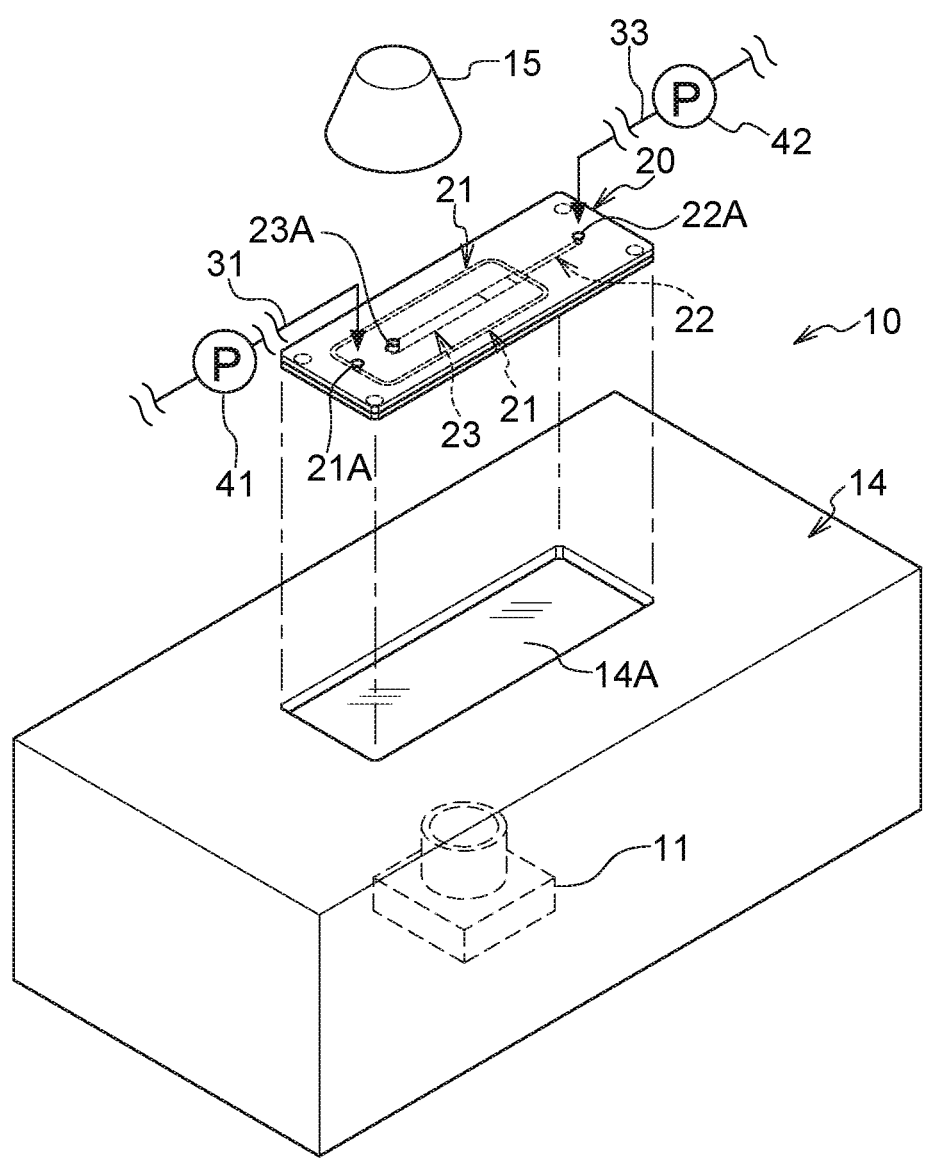
FIG. 2 is a perspective view schematically illustrating a positional relationship between a flow cell and a measurement device in an analysis device of the first exemplary embodiment of the present disclosure.

As illustrated in FIG. 2, the flow cell 20 is mounted to a recess 14A in a case 14 appropriate for the analysis device 10. A light source 15 and a camera that is an imaging device serving as the measurement device 11 are installed at positions facing each other across the confluent flow path 23 of the flow cell 20. The light source 15 radiates light beams onto the liquid sample 70 flowing through the confluent flow path 23. The camera serving as the measurement device 11 measures the liquid sample 70 flowing with the sheath fluid 80 by imaging the confluent flow path 23.

Figure 3:
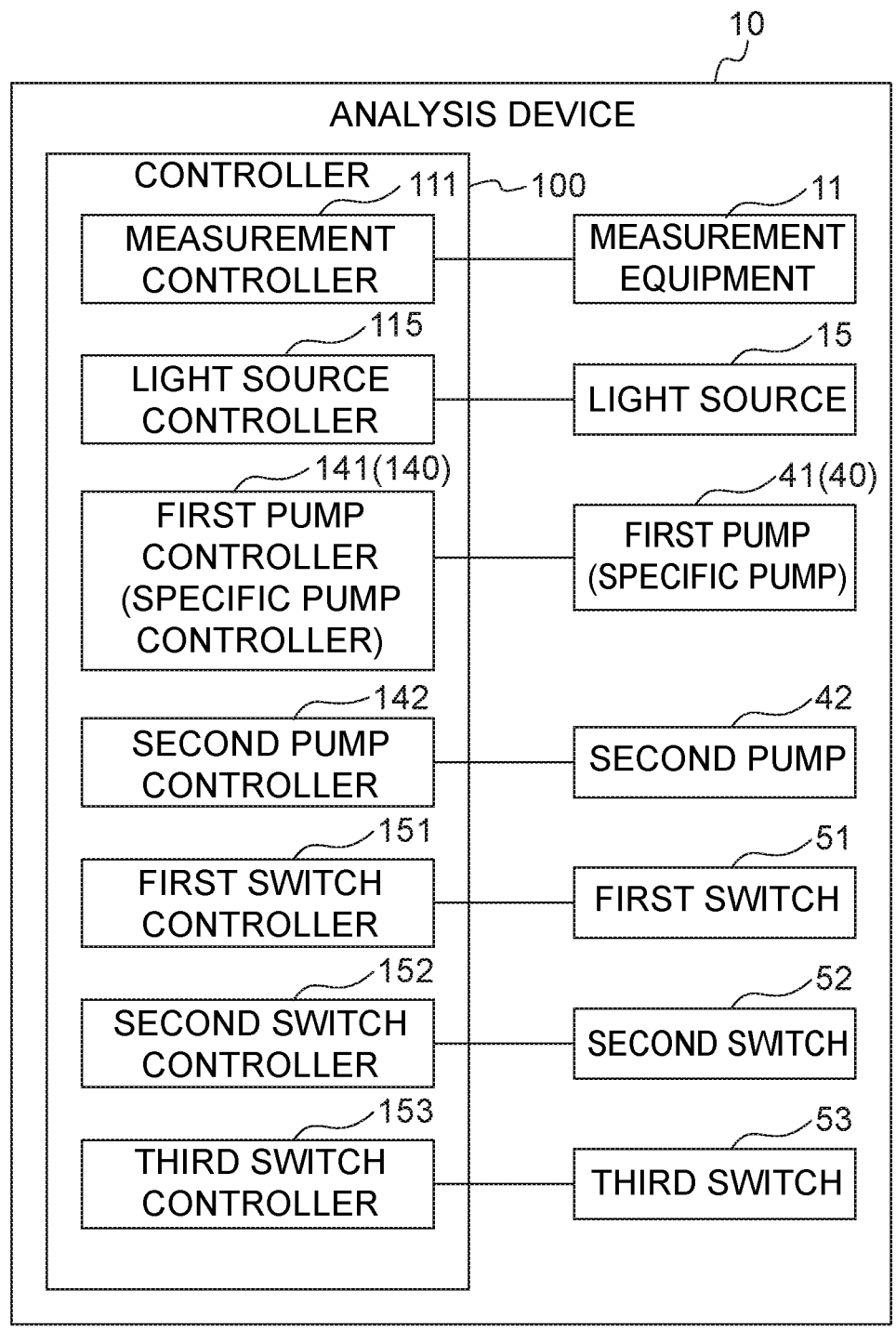
FIG. 3 is a functional block diagram of an analysis device of the first exemplary embodiment of the present disclosure.

FIG. 3 is a functional block diagram of the analysis device 10. The controller 100 controls each section of the analysis device 10. The controller 100 is configured by hardware as described later so as to function as the measurement controller 111 configured to control the measurement device 11, a light source controller 115 to control the light source 15, the first pump controller 141 serving as the specific pump controller 140 to control supply and aspiration of liquid by the first pump 41 serving as the specific pump 40, the second pump controller 142 to control supply and aspiration of liquid by the second pump 42, the first switch controller 151 configured to control flow path switching by the first switch 51, the second switch controller 152 configured to control flow path switching by the second switch 52, and the third switch controller 153 configured to control flow path switching by the third switch 53.

Figure 4:
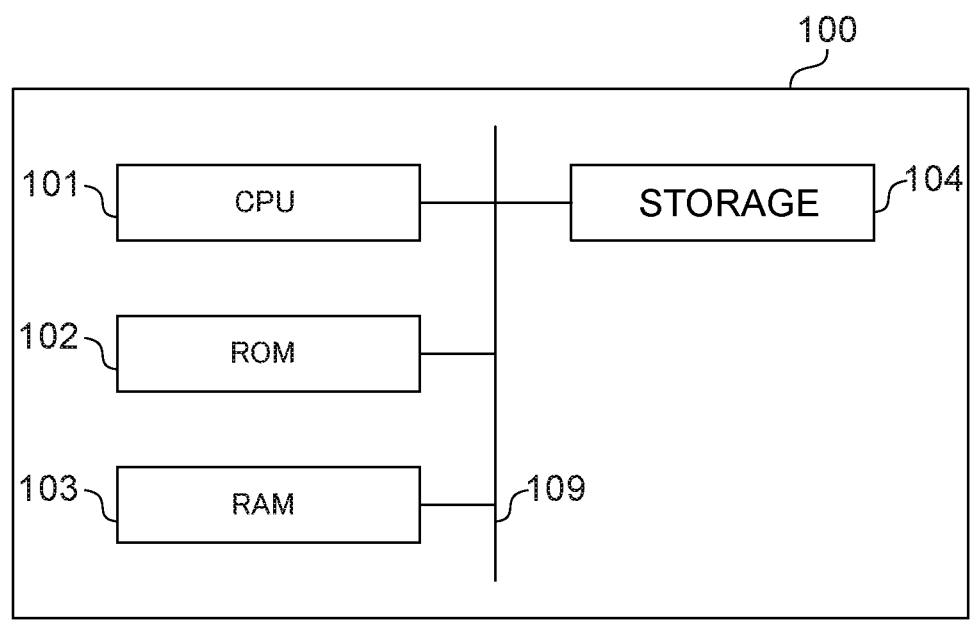
FIG. 4 is a block diagram illustrating a hardware configuration of a controller.

As illustrated by a hardware configuration in FIG. 4, the controller 100 includes a central processing unit (CPU) 101, read only memory (ROM) 102, random access memory (RAM) 103, and storage 104. The configuration elements are connected together via a bus 109 so as to be capable of communicating with each other.

The CPU 101 is a central processing unit and executes various programs and controls the configuration elements. Namely, the CPU 101 reads a program out from the ROM 102 or the storage 104, and executes the program using the RAM 103 as a workspace. The CPU 101 performs control of the configuration elements listed above and various computation processing according to the programs recorded in the ROM 102 or the storage 104.

The ROM 102 is stored with various programs and various data. The RAM 103 serves as a workspace for temporarily storing programs and data. The storage 104 is configured by a hard disk drive (HDD), a solid state drive (SSD), or a flash memory, and is stored with various programs including an operating system, and with various data. In the present exemplary embodiment, a program and various data related to measurement and determination is stored in the ROM 102 or the storage 104. Measurement data may also be saved in the storage 104.

Due to the CPU 101 in the hardware configuration described above executing the programs referred to, the controller 100 functions as the measurement controller 111, the light source controller 115, the first pump controller 141 (the specific pump controller 140), the second pump controller 142, the first switch controller 151, the second switch controller 152, and the third switch controller 153 of the analysis device 10, as illustrated in FIG. 3. A detailed explanation of these functions will be described below.

Operation of Analysis Device 10

The operation of the analysis device 10 of the present exemplary embodiment will now be described, with reference to the flowcharts of FIGS. 5A and 5B, and the schematic diagrams related to operation of FIGS. 6 to 12. Note that arrows appended in the vicinity of the lines in FIGS. 6 to 12 indicate the directions of flow of liquid (or gas). Moreover, the two directions colored black at each switch indicate the directions of communicating flow paths.

Figure 5A:
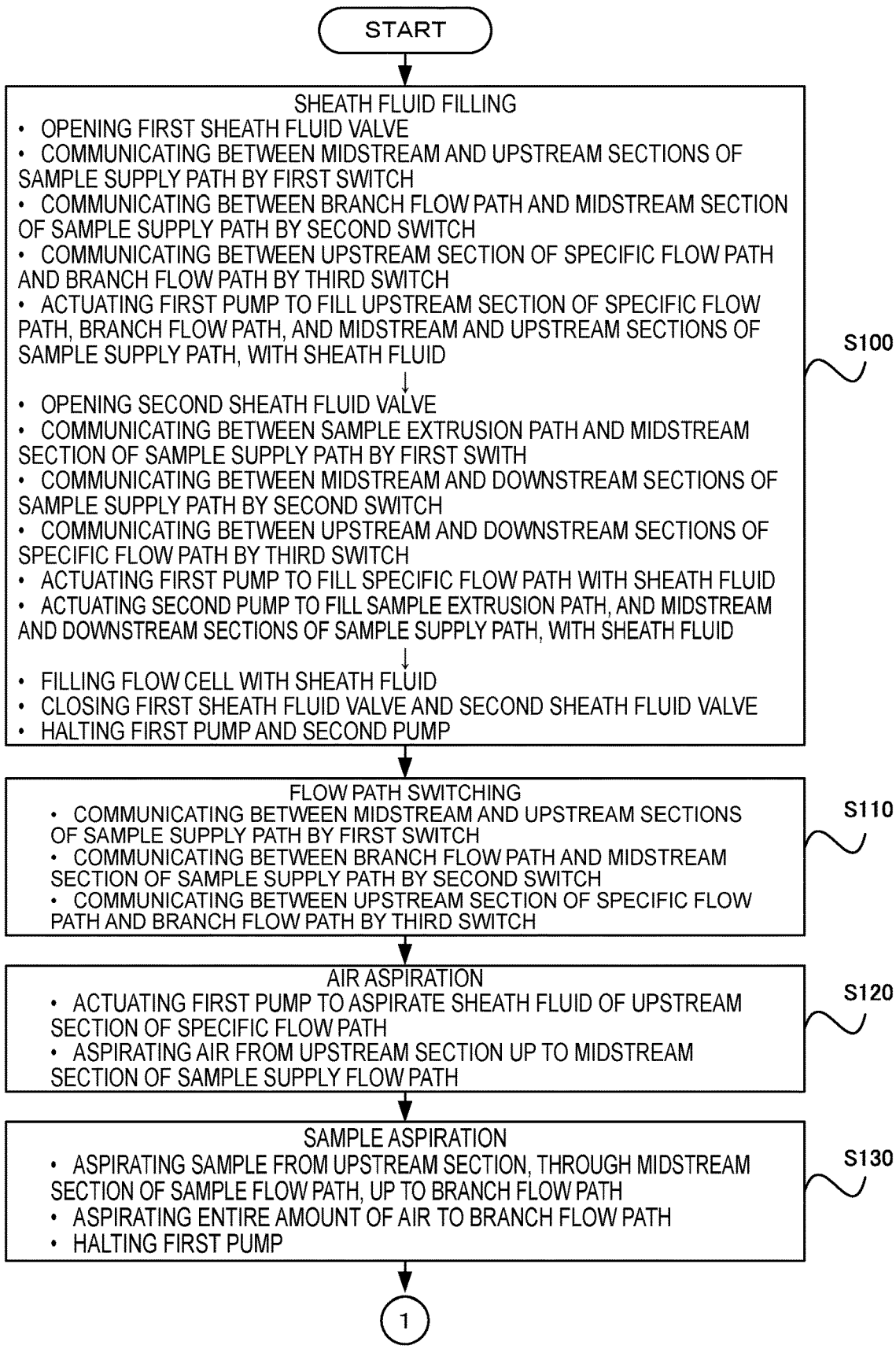
FIGS. 5A and 5B are flowcharts illustrating operation of an analysis device of the first exemplary embodiment of the present disclosure.
Figure 6:
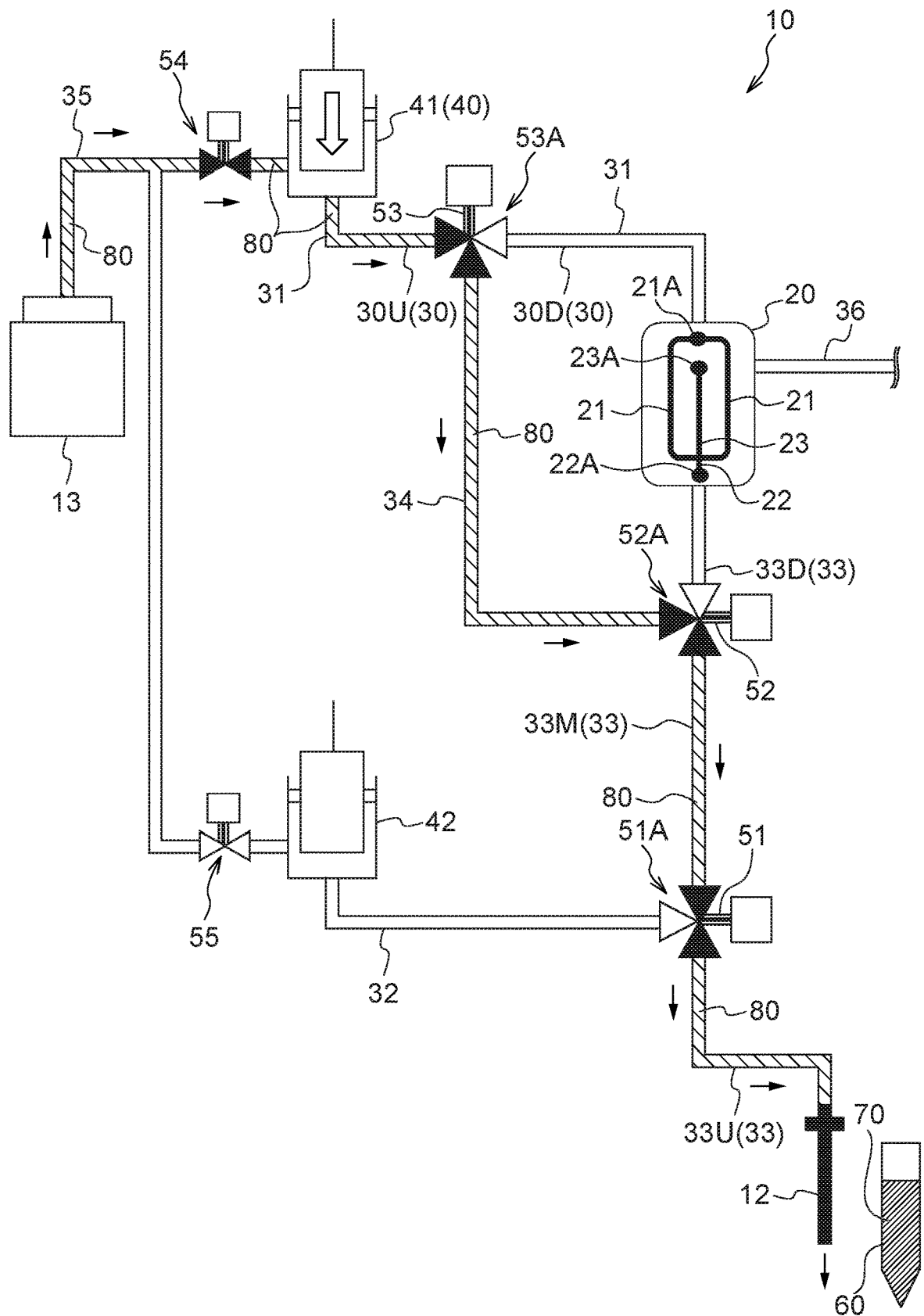
FIGS. 6 to 12 are schematic diagrams illustrating operation of an analysis device of the first exemplary embodiment of the present disclosure.

Prior to starting to use the analysis device 10, the lines of the analysis device 10 are filled with the sheath fluid 80 in a sheath fluid filling step S100 of FIG. 5A. First, as illustrated in FIG. 6, the first sheath fluid valve 54 is opened. Then the first switch controller 151 switches the flow paths of the first switch 51 so as to communicate the midstream section 33M with the upstream section 33U of the sample supply path 33, the second switch controller 152 switches the flow paths of the second switch 52 so as to communicate the branch flow path 34 with the midstream section 33M of the sample supply path 33, and the third switch controller 153 switches the flow paths of the third switch 53 so as to communicate the upstream section 30U of the sheath fluid supply path 31 (the specific flow path 30) with the branch flow path 34.

In this state, the first pump controller 141 serving as the specific pump controller 140 actuates the first pump 41 serving as the specific pump 40, and the sheath fluid 80 is supplied to the sheath fluid supply path 31 serving as the specific flow path 30. Thereby, the sheath fluid 80 supplied from the sheath fluid storage unit 13 into the first pump 41 via the first sheath fluid valve 54 passes from the first pump 41 through the third switch 53, the second switch 52, and the first switch 51, so as to reach the aspirator 12, and is discharged from the leading end thereof. Namely, the upstream section 30U of the sheath fluid supply path 31 (the specific flow path 30) from the first pump 41 to the third switch 53, the branch flow path 34, the midstream section 33M of the sample supply path 33 from the second switch 52 to the first switch 51, and the upstream section 33U of the sample supply path 33 from the first switch 51 to the aspirator 12, are all filled with the sheath fluid 80.

Figure 7:
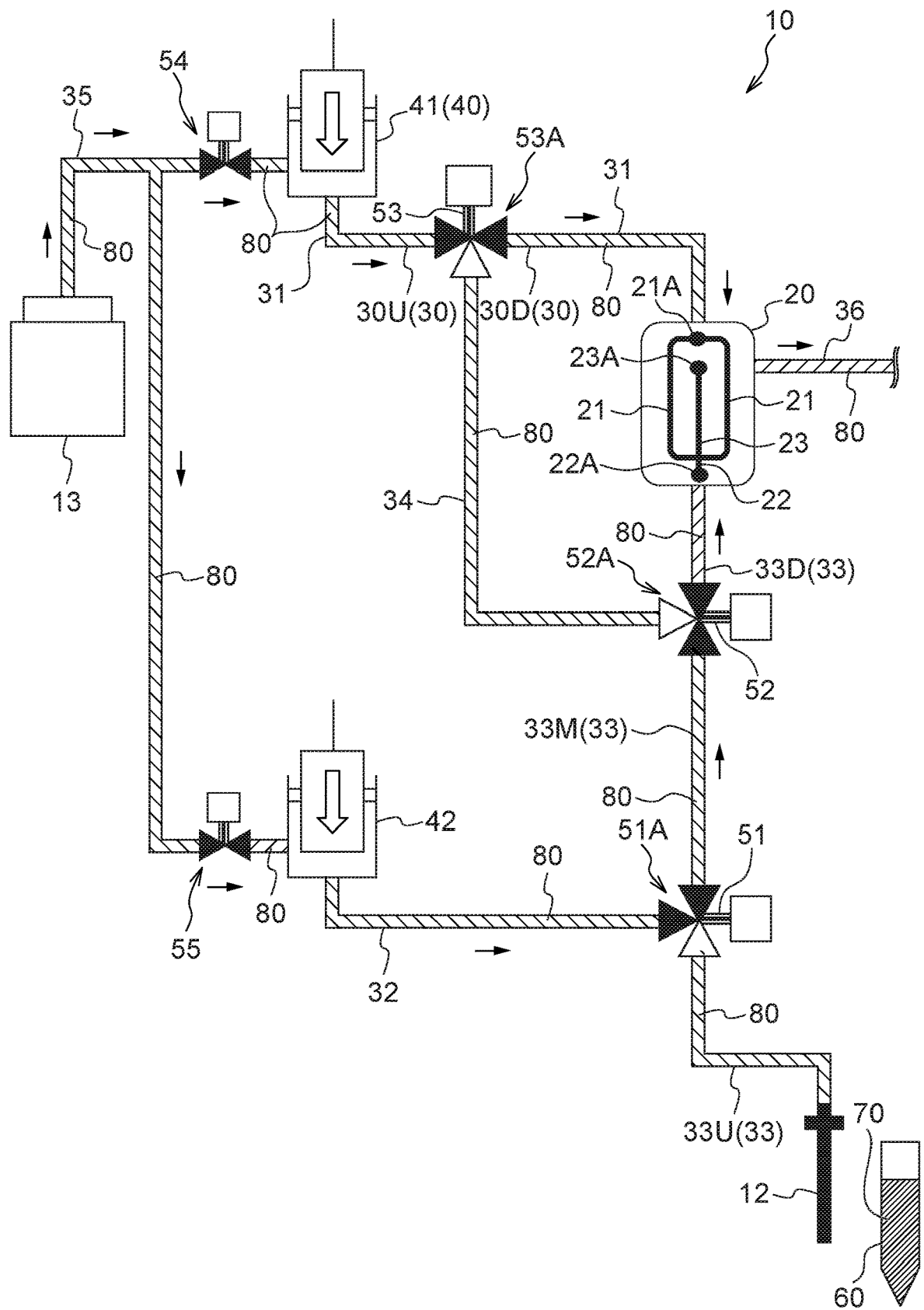

Next, as illustrated in FIG. 7, the second sheath fluid valve 55 is also opened together with the first sheath fluid valve 54. Then the first switch controller 151 switches the flow paths of the first switch 51 so as to communicate the sample extrusion path 32 with the midstream section 33M of the sample supply path 33, the second switch controller 152 switches the flow paths of the second switch 52 so as to communicate the midstream section 33M with the downstream section 33D of the sample supply path 33, and the third switch controller 153 switches the flow paths of the third switch 53 so as to communicate the upstream section 30U with the downstream section 30D of the specific flow path 30.

In this state the first pump controller 141 serving as the specific pump controller 140 actuates the first pump 41 serving as the specific pump 40, and the sheath fluid 80 is supplied to the sheath fluid supply path 31 serving as the specific flow path 30. Thereby, the sheath fluid 80 supplied from the sheath fluid storage unit 13 to the first pump 41 via the first sheath fluid valve 54 passes from the first pump 41 through the third switch 53 and reaches the sheath fluid port 21A of the flow cell 20. Namely, the sheath fluid supply path 31 from the first pump 41 to the sheath fluid port 21A of the flow cell 20 through the third switch 53 (i.e. the upstream section 30U and the downstream section 30D of the specific flow path 30) are all filled with the sheath fluid 80.

Simultaneously, the second pump controller 142 actuates the second pump 42 and the sheath fluid 80 is supplied to the sample extrusion path 32. Thereby, the sheath fluid 80 supplied from the sheath fluid storage unit 13 to the second pump 42 via the second sheath fluid valve 55 passes from the second pump 42 through the first switch 51 and the second switch 52, and reaches the sample port 22A of the flow cell 20. Namely, the sample extrusion path 32 from the second pump 42 to the first switch 51, the midstream section 33M of the sample supply path 33 from the first switch 51 to the second switch 52, and the downstream section 33D of the sample supply path 33 from the second switch 52 to the sample port 22A of the flow cell 20, are all filled with the sheath fluid 80.

Furthermore, in the flow cell 20, the sheath fluid 80 from the sheath fluid supply path 31 passes through the sheath fluid port 21A and fills the two branches of the sheath fluid flow path 21. On the other hand, the sheath fluid 80 from the sample supply path 33 passes through the sample port 22A and fills the sample flow path 22. Then, the sheath fluid 80 from both flows joins together in the confluent flow path 23, fills the confluent flow path 23, passes through the waste liquid port 23A, fills the waste liquid path 36, and is discharged to an external section, not illustrated in the drawings.

Thereby, the lines of the analysis device 10 are filled with the sheath fluid 80. In other words, the flow cell 20, a sample supply path 33, and an aspirator 12 are filled with the sheath fluid 80. Then, the first sheath fluid valve 54 and the second sheath fluid valve 55 are both closed. The first pump controller 141 and the second pump controller 142 then respectively halt the actuation of the first pump 41 and the second pump 42.

Figure 8:
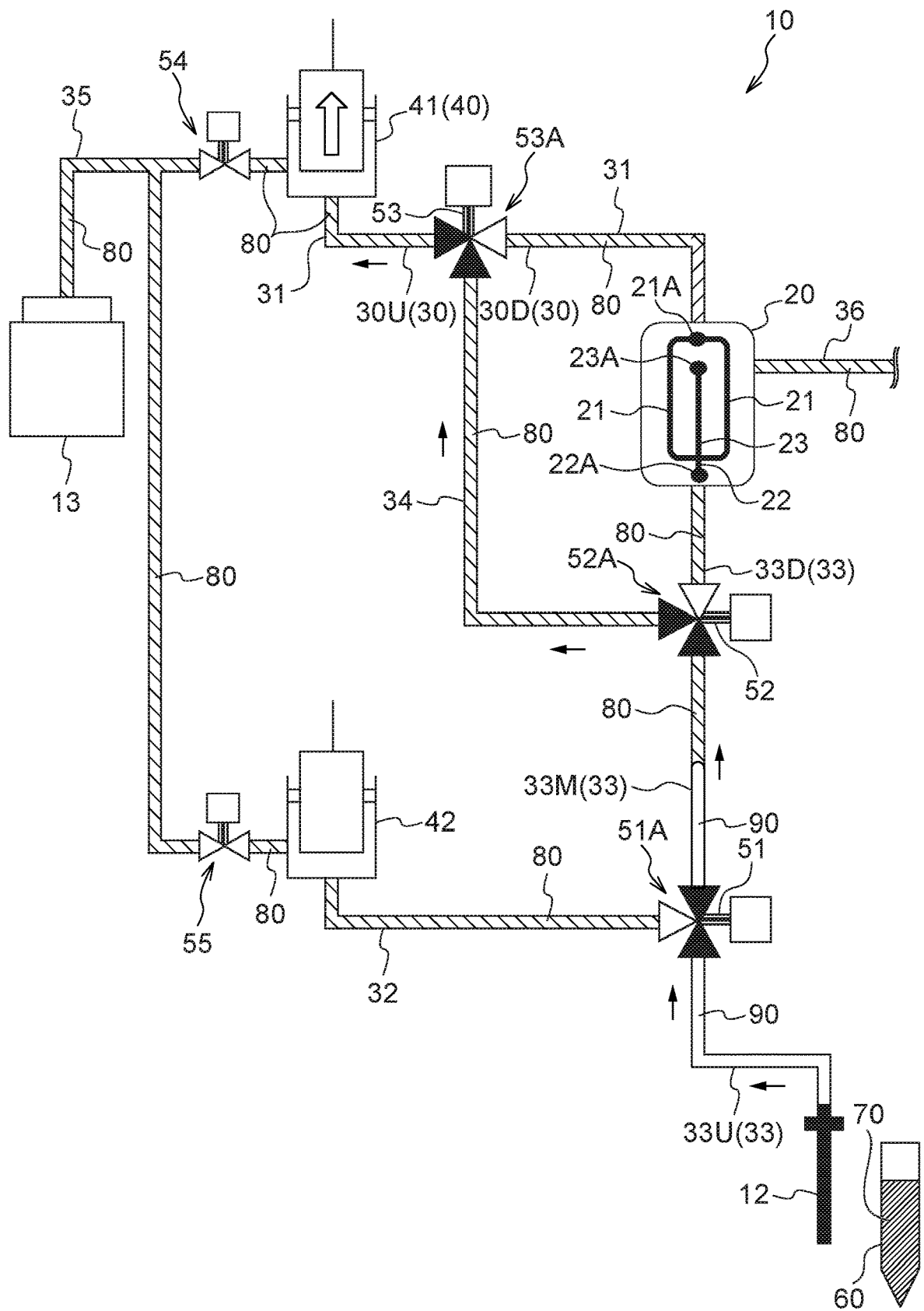

Then, at a flow path switching step S110 of FIG. 5A, as illustrated in FIG. 8, the first switch controller 151 switches the flow paths of the first switch 51 so as to communicate the upstream section 33U with the midstream section 33M of the sample supply path 33, the second switch controller 152 switches the flow paths of the second switch 52 so as to communicate the midstream section 33M of the sample supply path 33 with the branch flow path 34, and the third switch controller 153 switches the flow paths of the third switch 53 so as to communicate the branch flow path 34 with the upstream section 30U of the specific flow path 30.

In this state, at an air aspiration step S120 of FIG. 5A, the first pump controller 141 serving as the specific pump controller 140 actuates the first pump 41 serving as the specific pump 40 so as to impart a negative pressure to the upstream section 30U of the sheath fluid supply path 31 serving as the specific flow path 30, and the sheath fluid 80 is aspirated from the upstream section 30U of the sheath fluid supply path 31 serving as the specific flow path 30. Thereby, the air 90 is aspirated from the aspirator 12. The aspirated air 90 passes from the upstream section 33U of the sample supply path 33, and reaches the midstream section 33M of the sample supply path 33 between the first switch 51 and the second switch 52.

Figure 9:
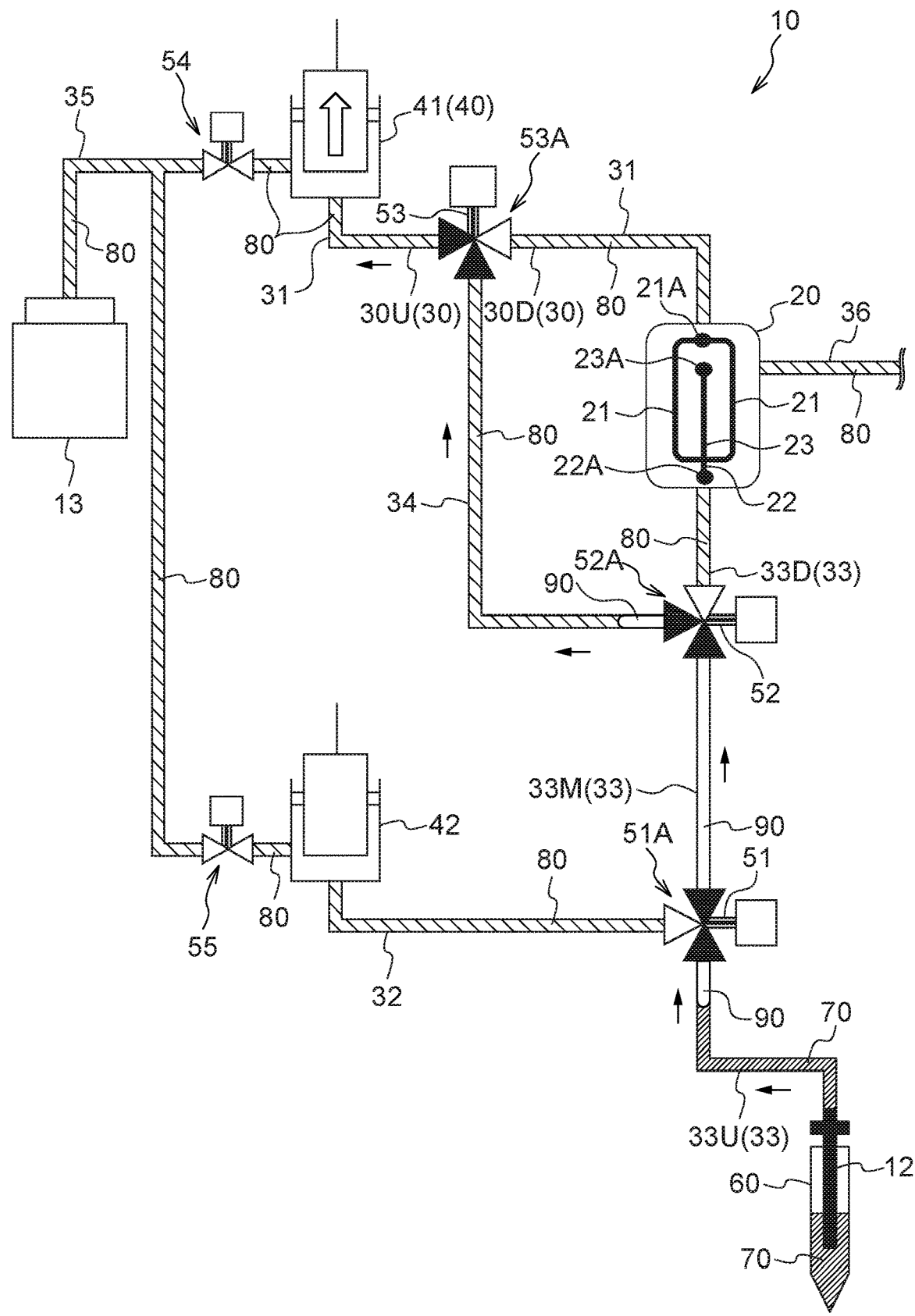

Then, at a sample aspiration step S130 of FIG. 5A, while maintaining the operation state of FIG. 8 and continuing to impart negative pressure to the upstream section 30U of the sheath fluid supply path 31 serving as the specific flow path 30, when the aspirator 12 is dipped in the liquid sample 70 contained in the sample container 60 as illustrated in FIG. 9, the liquid sample 70 is aspirated from the aspirator 12 into the upstream section 33U of the sample supply path 33. On the other hand, as illustrated in FIG. 9, the aspirated air 90 passes through the second switch 52 and reaches the branch flow path 34. The aspirated air 90 described above is interposed between the sheath fluid 80 filling the aspirator 12, and the liquid sample 70 aspirated by the aspirator 12, so that the sheath fluid 80 does not directly contact the liquid sample 70.

Figure 10:
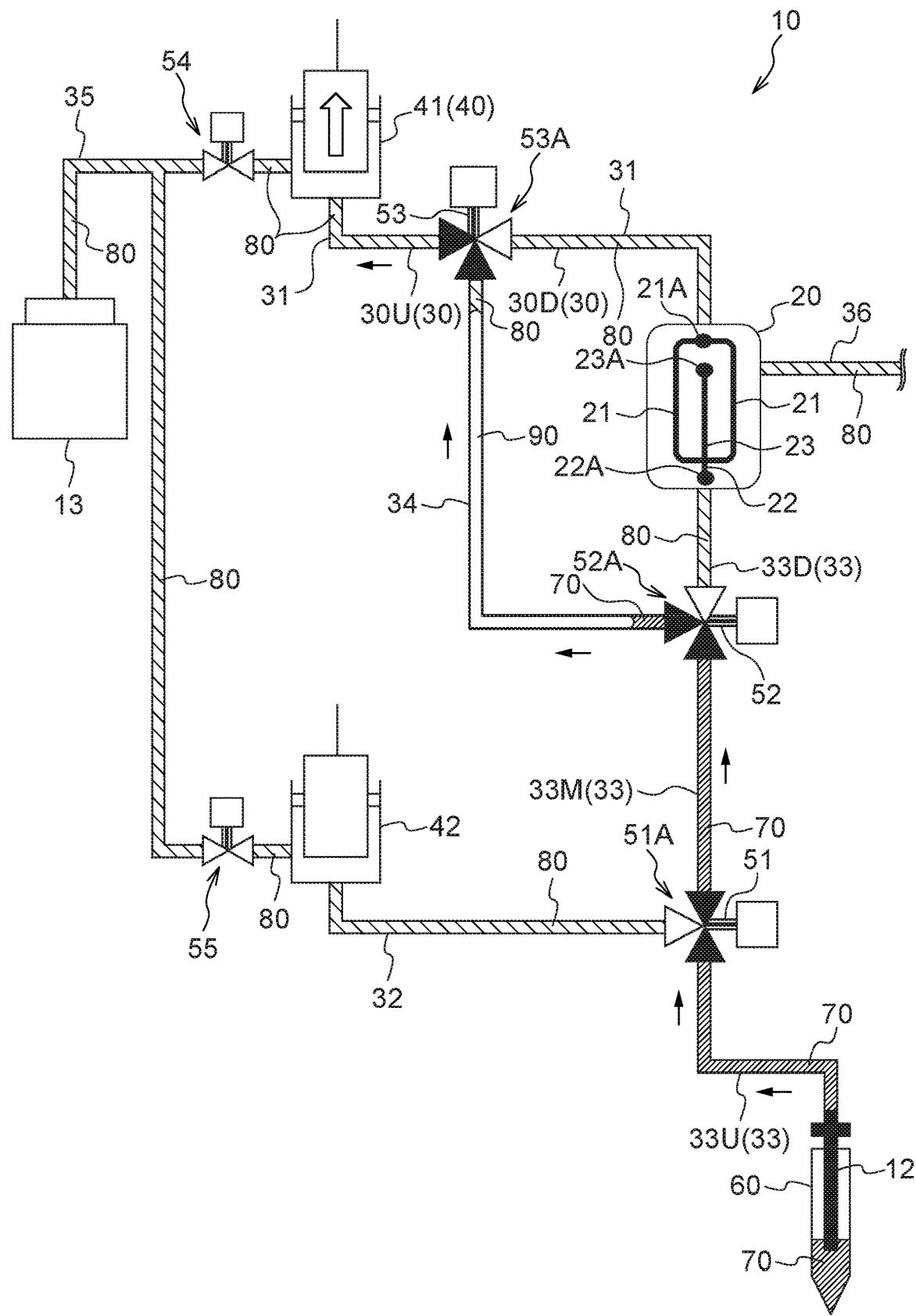

Next, as illustrated in FIG. 10, the entire amount of the aspirated air 90 passes the second switch 52 and reaches the branch flow path 34, the liquid sample 70 simultaneously aspirated reaches the midstream section 33M of the sample supply path 33, and a portion of the liquid sample 70 passes through the second switch 52 and reaches the branch flow path 34. Then, the first pump controller 141 serving as the specific pump controller 140 halts actuation of the first pump 41 serving as the specific pump 40, and stops imparting the negative pressure to the upstream section 30U of the sheath fluid supply path 31 serving as the specific flow path 30. Thereby, the entire amount of the aspirated air 90 is shunted to the branch flow path 34 and accommodated inside the branch flow path 34.

Figure 5B:
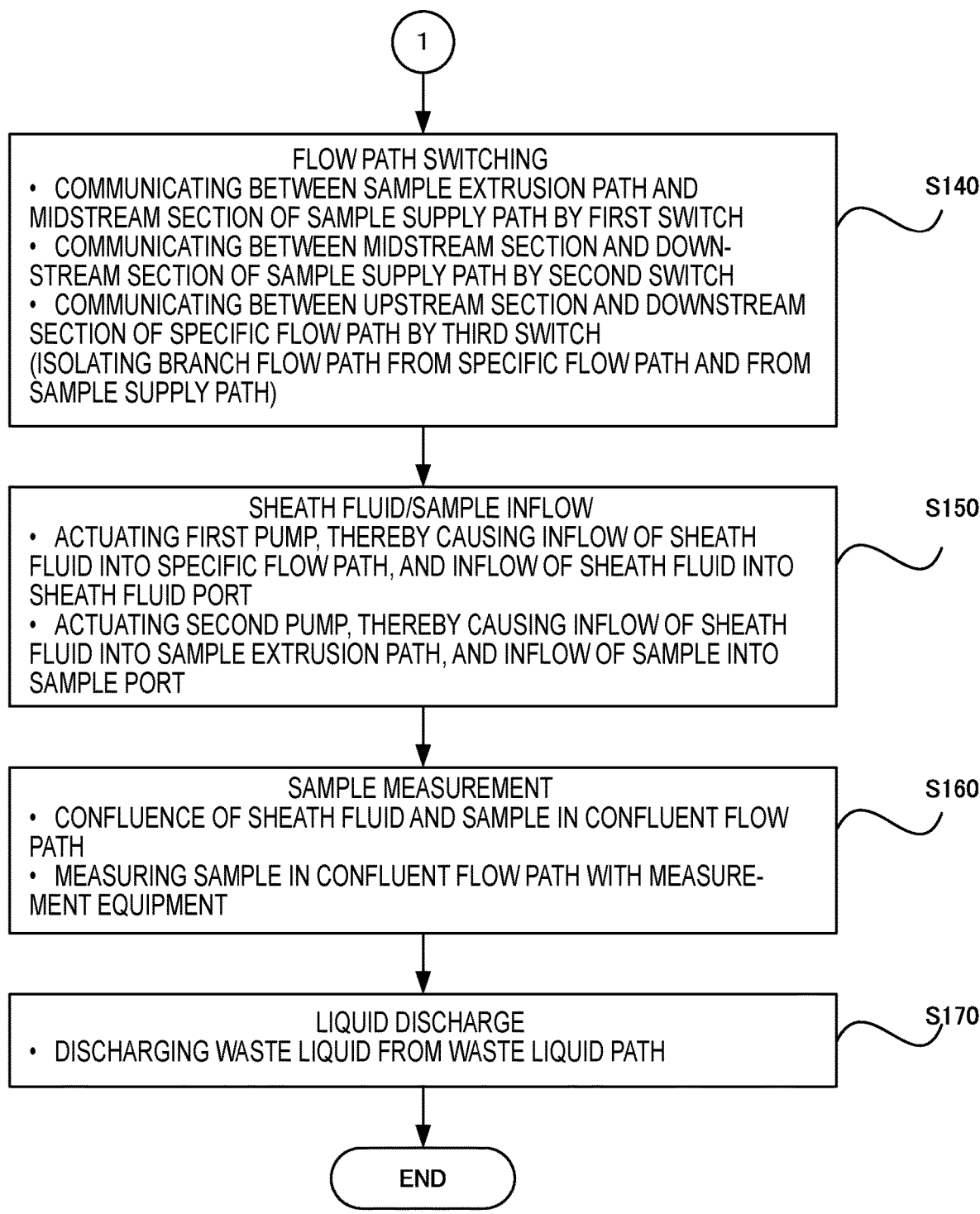
Figure 11:
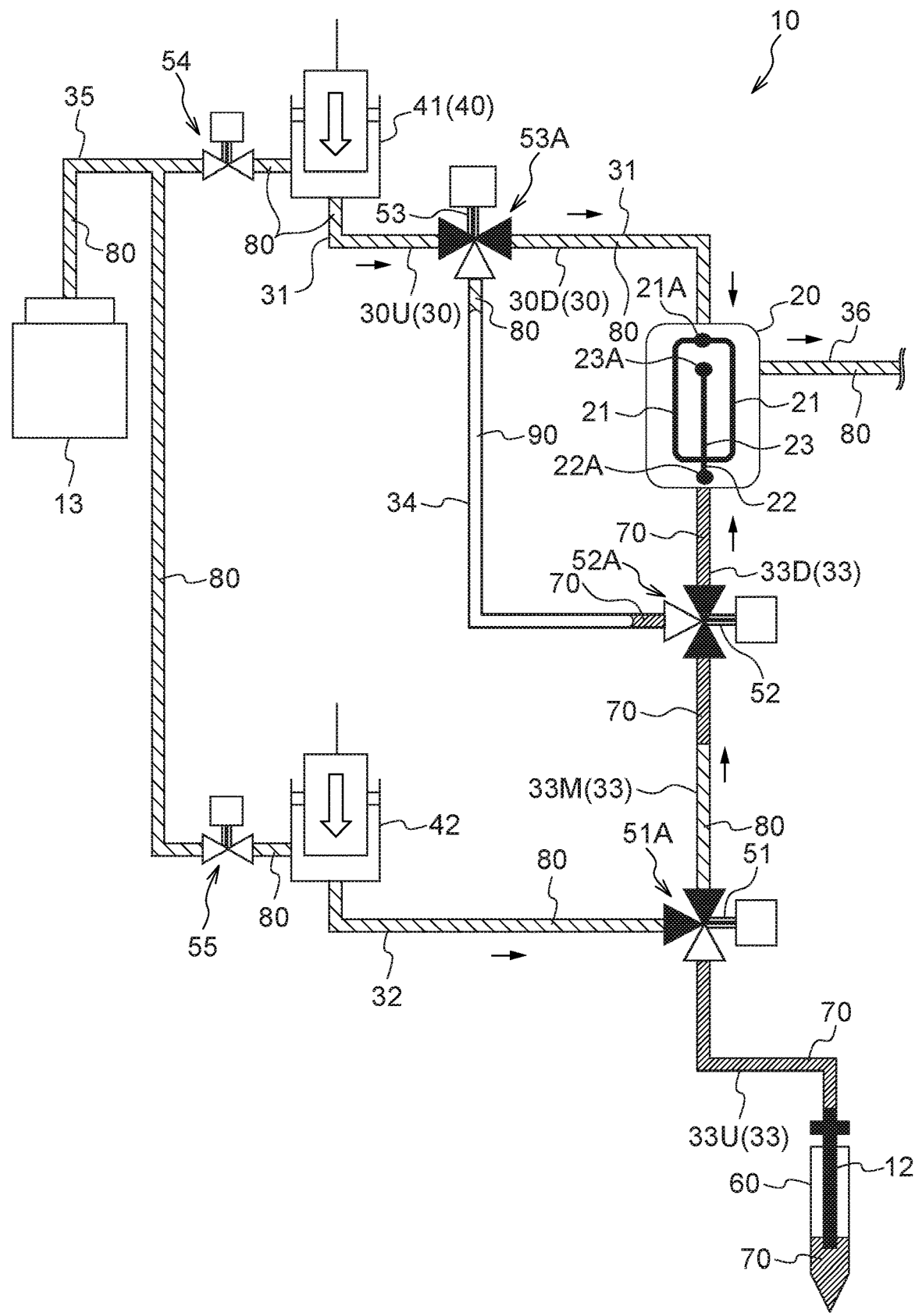

Then, at a flow path switching step S140 of FIG. 5B, as illustrated in FIG. 11, the first switch controller 151 switches the flow paths of the first switch 51 so as to communicate the sample extrusion path 32 with the midstream section 33M of the sample supply path 33, the second switch controller 152 switches the flow paths of the second switch 52 so as to communicate the midstream section 33M with the downstream section 33D of the sample supply path 33, and the third switch controller 153 switches the flow paths of the third switch 53 so as to communicate the upstream section 30U with the downstream section 30D of the specific flow path 30. Thereby, the entire amount of the aspirated air 90 is sealed inside the branch flow path 34.

In this state, at a sheath fluid/sample inflow step S150 of FIG. 5B, the first pump controller 141 serving as the specific pump controller 140 actuates the first pump 41 serving as the specific pump 40 so as to impart a positive pressure to the sheath fluid supply path 31 serving as the specific flow path 30, and the sheath fluid 80 is supplied again to the sheath fluid supply path 31. Thereby, the sheath fluid 80 flows through the upstream section 30U of the specific flow path 30 from the first pump 41 to the third switch 53, and through the downstream section 30D of the specific flow path 30 from the third switch 53, and then into the sheath fluid port 21A of the flow cell 20.

Simultaneously, the second pump controller 142 actuates the second pump 42 so as to impart a positive pressure to the sample extrusion path 32, and the sheath fluid 80 is supplied again to the sample extrusion path 32. Thereby, the sheath fluid 80, passing through the sample extrusion path 32 from the second pump 42 to the first switch 51, reaches the midstream section 33M of the sample supply path 33, extrudes the liquid sample 70 aspirated in this location, and causes the liquid sample 70 to flow from the second switch 52, through the downstream section 33D of the sample supply path 33, to the sample port 22A of the flow cell 20.

Figure 12:
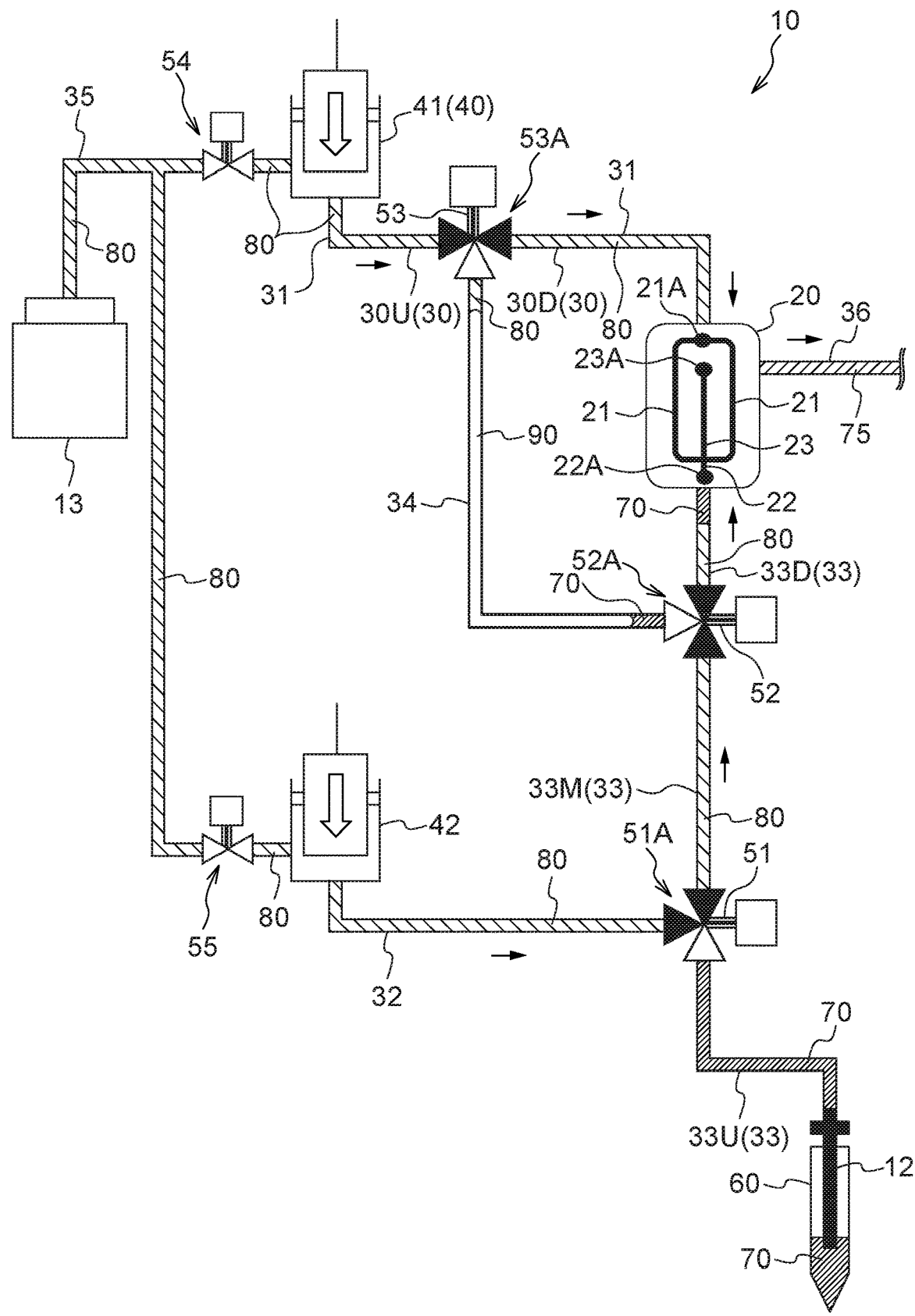

Then, at a sample measurement step S160 of FIG. 5B, as illustrated in FIG. 12, at the time when the sheath fluid 80 flowing from the sample extrusion path 32, passing the second switch 52, reaches the downstream section 33D of the sample supply path 33, urine as the liquid sample 70 that flows from the sample port 22A of the flow cell 20 to the sample flow path 22 joins the sheath fluid 80 that flows from the two paths of the sheath fluid flow path 21, and reaches the confluent flow path 23. The urine as the liquid sample 70 is measured by illumination from the light source 15, having a light intensity adjusted by the light source controller 115, with the camera serving as the measurement device 11 controlled by the measurement controller 111. Namely, discrimination of types of formed elements present in the urine and measurement of amounts of the formed elements in the urine are performed using outlines and sizes of objects appearing in images taken by the camera. Note that a waste liquid 75 that is a mixture of the liquid sample 70 and the sheath fluid 80 in the confluent flow path 23 is, at a waste liquid discharge step S170 of FIG. 5B, discharged from the waste liquid port 23A, through the waste liquid path 36, to an external section, not illustrated in the drawings.

Note that a portion of the liquid sample 70 that contacts the sheath fluid 80 delivered by the second pump 42, that is, an end portion of the liquid sample 70 that is the last portion to flow into the flow cell 20, is diluted by the sheath fluid 80. Thus, it is preferable that the measurement controller 111 may complete the measurement before the portion reach the measurement device 11.

Note that the first pump 41 and the second pump 42 may employ pumps having the same capacity, however, if pumps of different capacity are employed therefor, then it is preferable that the pump having the larger capacity is employed for the first pump 41 serving as the specific pump 40 to aspirate the sheath fluid 80 from the specific flow path 30.

Moreover, it is necessary to determine an internal diameter and a length of the branch flow path 34 so that a volume of the branch flow path 34 exceeds a volume of the air 90 aspirated from the aspirator 12. Furthermore, in a case in which a portion of the aspirated liquid sample 70 is caused to reach the branch flow path 34 as illustrated in FIG. 11, it is necessary to determine the volume of the branch flow path 34 so that the volume exceeds a sum of the volume of the air 90 aspirated from the aspirator 12 and the volume of the portion of the aspirated liquid sample 70. Note that portions of the aspirated liquid sample 70 in close proximity to the air 90 are sometimes diluted by sheath fluid 80 remaining in the flow path, and sometimes contain dirt from the flow path. Thus, it is preferable for the portion of the aspirated liquid sample 70 not to flow into the flow cell by causing the portion to reach the branch flow path 34 so that that portion is sealed therein.

Second Exemplary Embodiment

Figure 13:
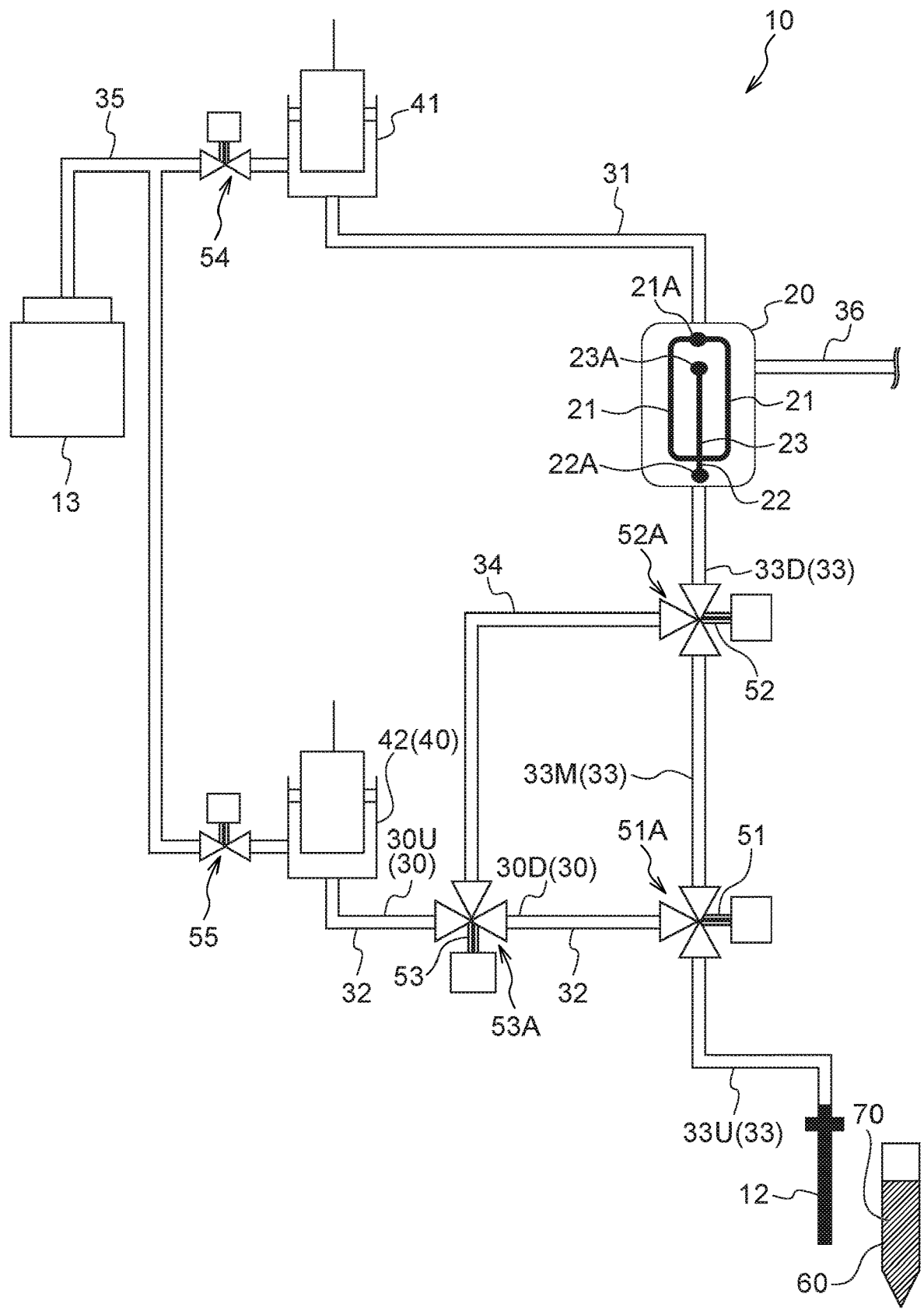
FIG. 13 is a schematic diagram of an analysis device of a second exemplary embodiment of the present disclosure.

FIG. 13 schematically illustrates a second exemplary embodiment of the analysis device 10 that employs urine as the liquid sample 70 and analyzes formed elements in the urine. The second exemplary embodiment differs from the first exemplary embodiment in that the third switch 53 is provided on the sample extrusion path 32, and the branch flow path 34 interconnects the sample supply path 33 and the sample extrusion path 32. In the present exemplary embodiment, similarly to in the first exemplary embodiment, the sheath fluid supply path 31 and the sample supply path 33 are connected to the flow cell 20 as flow paths flowing into the flow cell 20. Moreover, the waste liquid path 36 is also connected to the flow cell 20 as a flow path flowing out from the flow cell 20. For convenience the second exemplary embodiment will be described for a case in which the analysis device 10 is employed for analyzing formed elements in urine, however the liquid sample 70 of the second exemplary embodiment is not limited to urine.

Configuration of Analysis Device 10

The configuration of the flow cell 20 is similar to that of the first exemplary embodiment. Namely, the sheath fluid supply path 31 is connected to the sheath fluid port 21A of the flow cell 20. The sample supply path 33 is connected to the sample port 22A. The waste liquid path 36 is connected to the waste liquid port 23A.

The aspirator 12 is formed as a nozzle with a leading end fitted to the most upstream end of the sample supply path 33. The aspirator 12 is a configuration element to aspirate the liquid sample 70 from a sample container 60 containing the liquid sample 70 using the second pump 42 serving as the specific pump 40, as described later. The first branch point 51A is set partway along the sample supply path 33, at which the first switch 51 configured by a three-way valve is provided. The sample extrusion path 32 is connected to the sample supply path 33 via the first switch 51. In other words, the sample extrusion path 32 joins the sample supply path 33 at the first branch point 51A.

The sheath fluid 80 (see FIG. 6 to FIG. 12) is supplied from the first pump 41 into the sheath fluid supply path 31. Moreover, the sheath fluid 80 is also supplied from the second pump 42 into the sample extrusion path 32. In the present exemplary embodiment, plunger pumps are employed for both the first pump 41 and the second pump 42, enabling the sheath fluid 80 to also be aspirated from the sheath fluid supply path 31 and the sample extrusion path 32. Note that although the second pump 42 functions as the specific pump 40 in the present exemplary embodiment as described later, the first pump 41 not serving as the specific pump 40 may employ a pump, such as a tube pump, that only has a fluid delivery function and does not have an aspiration function.

The sheath fluid storage unit 13, the sheath fluid transport path 35, the first sheath fluid valve 54, and the second sheath fluid valve 55 are all similar to in the first exemplary embodiment.

Note that also in the present exemplary embodiment, similar to in the first exemplary embodiment, a side closer to the flow cell 20 in each of the sheath fluid supply path 31, the sample extrusion path 32, and the sample supply path 33 is defined as a downstream side, and an opposite side thereto is defined as an upstream side.

The second branch point 52A is also set on the sample supply path 33 between the first branch point 51A and the sample port 22A of the flow cell 20 (in other words, at the downstream side of the first branch point 51A), at which the second switch 52 configured by a three-way valve is provided. On the other hand, the third branch point 53A is set partway along the sample extrusion path 32 (in other words between the second pump 42 and the first branch point 51A), at which the third switch 53 configured by a three-way valve is provided. Further, the second branch point 52A and the third branch point 53A are interconnected by the branch flow path 34.

Note that the sample extrusion path 32 on which the third branch point 53A is provided is also referred to as the specific flow path 30. The second pump 42 to supply the sheath fluid 80 to the sample extrusion path 32 serving as the specific flow path 30 is also referred to as the specific pump 40.

The sheath fluid supply path 31, the sample extrusion path 32, the sample supply path 33, and the branch flow path 34, as well as the sheath fluid transport path 35 and the waste liquid path 36, are, similarly to in the first exemplary embodiment, all configured by flexible and soft tubing (for example, TEFLON (registered trademark) tube).

The sample supply path 33 is divided into three parts by the first branch point 51A and the second branch point 52A, and, similar to in the first exemplary embodiment, the part of upstream side from the first branch point 51A is referred to as an upstream section 33U, the part between the first branch point 51A and the second branch point 52A is referred to as a midstream section 33M, and the part between the second branch point 52A and the sample port 22A is referred to as downstream section 33D. In other words, the upstream section 33U and the midstream section 33M of the sample supply path 33 and the sample extrusion path 32 join together at the first branch point 51A. Moreover, the midstream section 33M and the downstream section 33D of the sample supply path 33 and the branch flow path 34 join together at the second branch point 52A.

Furthermore, in the present exemplary embodiment, the sample extrusion path 32 serving as the specific flow path 30 is divided into two parts by the third branch point 53A, and the part of the upstream side from the third branch point 53A is referred to as an upstream section 30U, and the part of the downstream side from the third branch point 53A is referred to as a downstream section 30D. In other words, the upstream section 30U and the downstream section 30D of the specific flow path 30 and the branch flow path 34 join together at the third branch point 53A.

The positional relationships of the flow cell 20, the light source 15 and the measurement device 11 are similar to those in the first exemplary embodiment as illustrated in FIG. 2. The meaning of measurement of the liquid sample 70 is also similar thereto.

Figure 14:
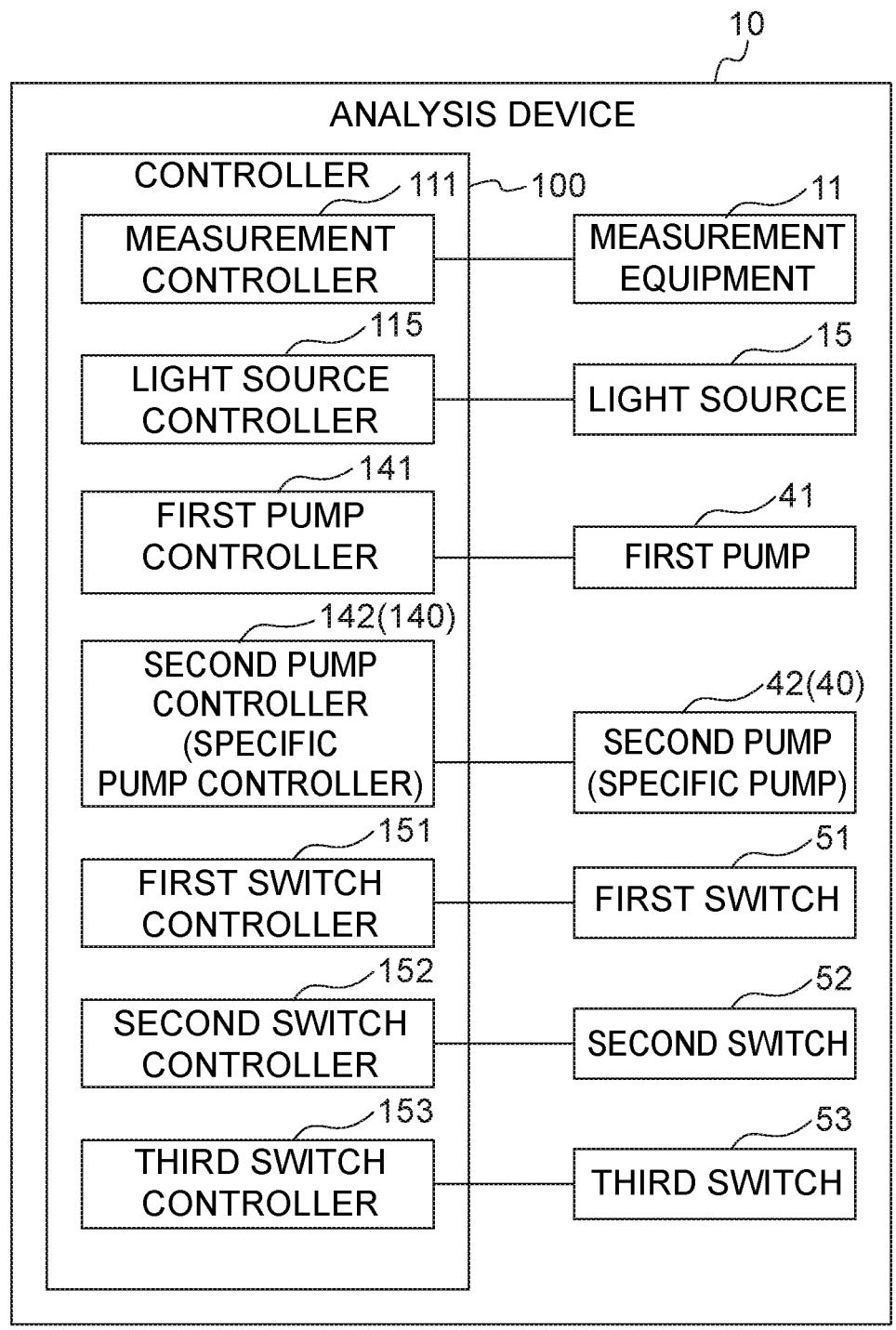
FIG. 14 is a functional block diagram of an analysis device of the second exemplary embodiment of the present disclosure.

FIG. 14 is a functional block diagram of the analysis device 10. The controller 100 controls each section of the analysis device 10. The controller 100 is configured by hardware as described later so as to function as the measurement controller 111 configured to control the measurement device 11, the light source controller 115 to control the light source 15, the first pump controller 141 configured to control supply and aspiration of liquid by the first pump 41, the second pump controller 142 serving as the specific pump controller 140 configured to control supply and aspiration of liquid by the second pump 42 serving as the specific pump 40, the first switch controller 151 configured to control flow path switching by the first switch 51, the second switch controller 152 to configured control flow path switching by the second switch 52, and the third switch controller 153 configured to control flow path switching by the third switch 53.

Note that a hardware configuration of the controller 100 is similar to that of the first exemplary embodiment, as illustrated in FIG. 4. Due to the CPU 101 in the hardware configuration described above executing the programs referred to above, the controller 100 functions as the measurement controller 111, the light source controller 115, the first pump controller 141, the second pump controller 142 (the specific pump controller 140), the first switch controller 151, the second switch controller 152, and the third switch controller 153 of the analysis device 10, as illustrated in FIG. 14. A detailed explanation of these functions will be described later.

Operation of Analysis Device 10

The operation of the analysis device 10 of the present exemplary embodiment will now be described, with reference to the flowcharts of FIGS. 15A and 15B, and the schematic diagrams related to operation of FIGS. 16 to 22. Note that arrows appended in the vicinity of the lines in FIGS. 16 to 22 indicate the directions of flow of liquid (or gas). Moreover, the two directions colored black at each switch indicate the directions of communicating flow paths.

Figure 16:
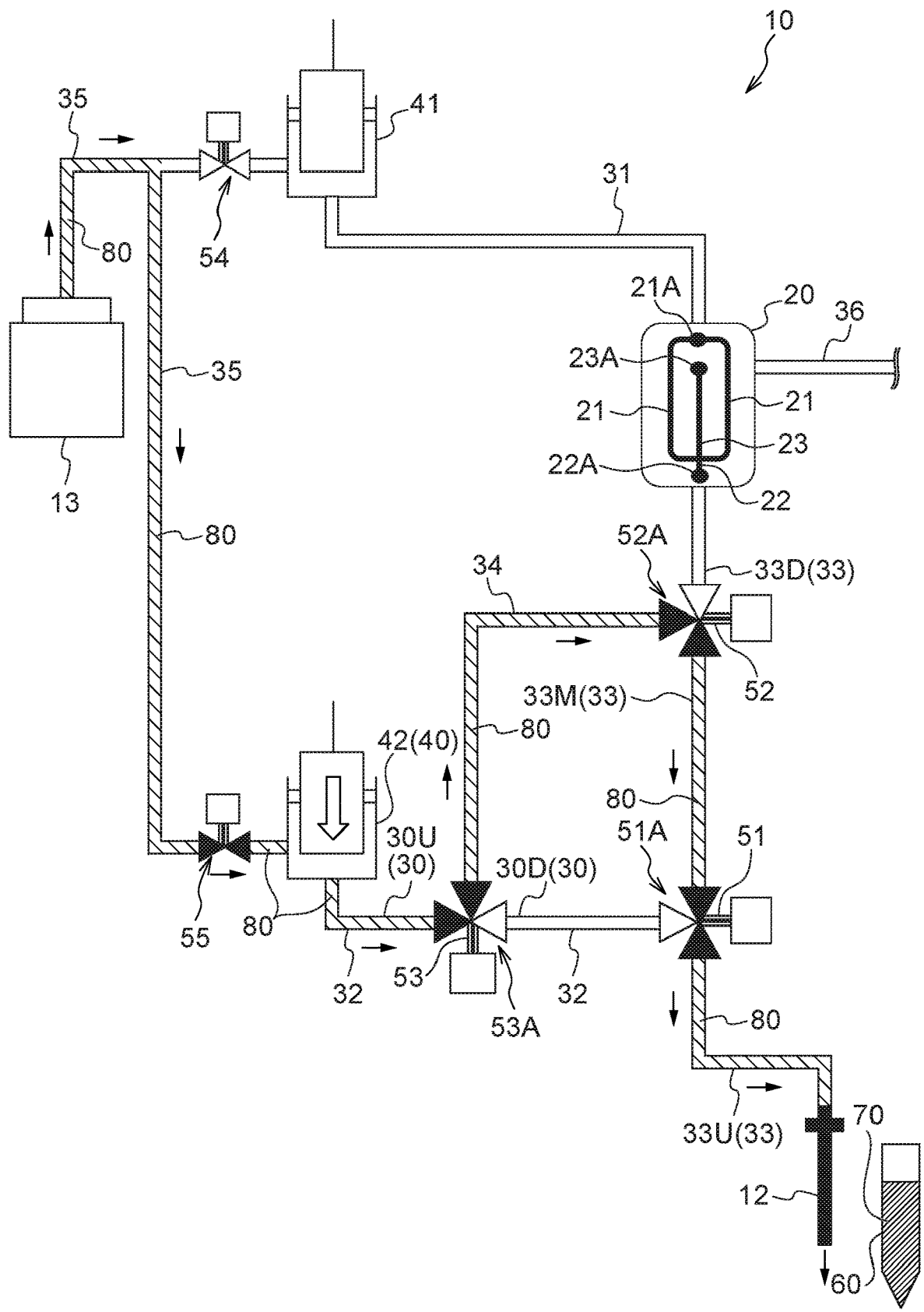
FIGS. 16 to 22 are schematic diagrams illustrating operation of an analysis device of the second exemplary embodiment of the present disclosure.

Prior to starting to use the analysis device 10, the lines of the analysis device 10 are filled with the sheath fluid 80 in a sheath fluid filling step S200 of FIG. 15A. First, as illustrated in FIG. 16, the second sheath fluid valve 55 is opened. Then the first switch controller 151 switches the flow paths of the first switch 51 so as to communicate the midstream section 33M with the upstream section 33U of the sample supply path 33, the second switch controller 152 switches the flow paths of the second switch 52 so as to communicate the branch flow path 34 with the midstream section 33M of the sample supply path 33, and the third switch controller 153 switches the flow paths of the third switch 53 so as to communicate the upstream section 30U of sample extrusion path 32 with the branch flow path 34.

In this state, the second pump controller 142 serving as the specific pump controller 140 actuates the second pump 42 serving as the specific pump 40, and the sheath fluid 80 is supplied to the sample extrusion path 32 serving as the specific flow path 30. Thereby, the sheath fluid 80 supplied from the sheath fluid storage unit 13 into the second pump 42 via the second sheath fluid valve 55 passes from the second pump 42 through the third switch 53, the second switch 52, and the first switch 51, so as to reach the aspirator 12, and is discharged from the leading end thereof. Namely, the upstream section 30U of the sample extrusion path 32 (the specific flow path 30) from the second pump 42 to the third switch 53, the branch flow path 34, the midstream section 33M of the sample supply path 33 from the second switch 52 to the first switch 51, and the upstream section 33U of the sample supply path 33 from the first switch 51 to the aspirator 12, are all filled with the sheath fluid 80.

Figure 17:
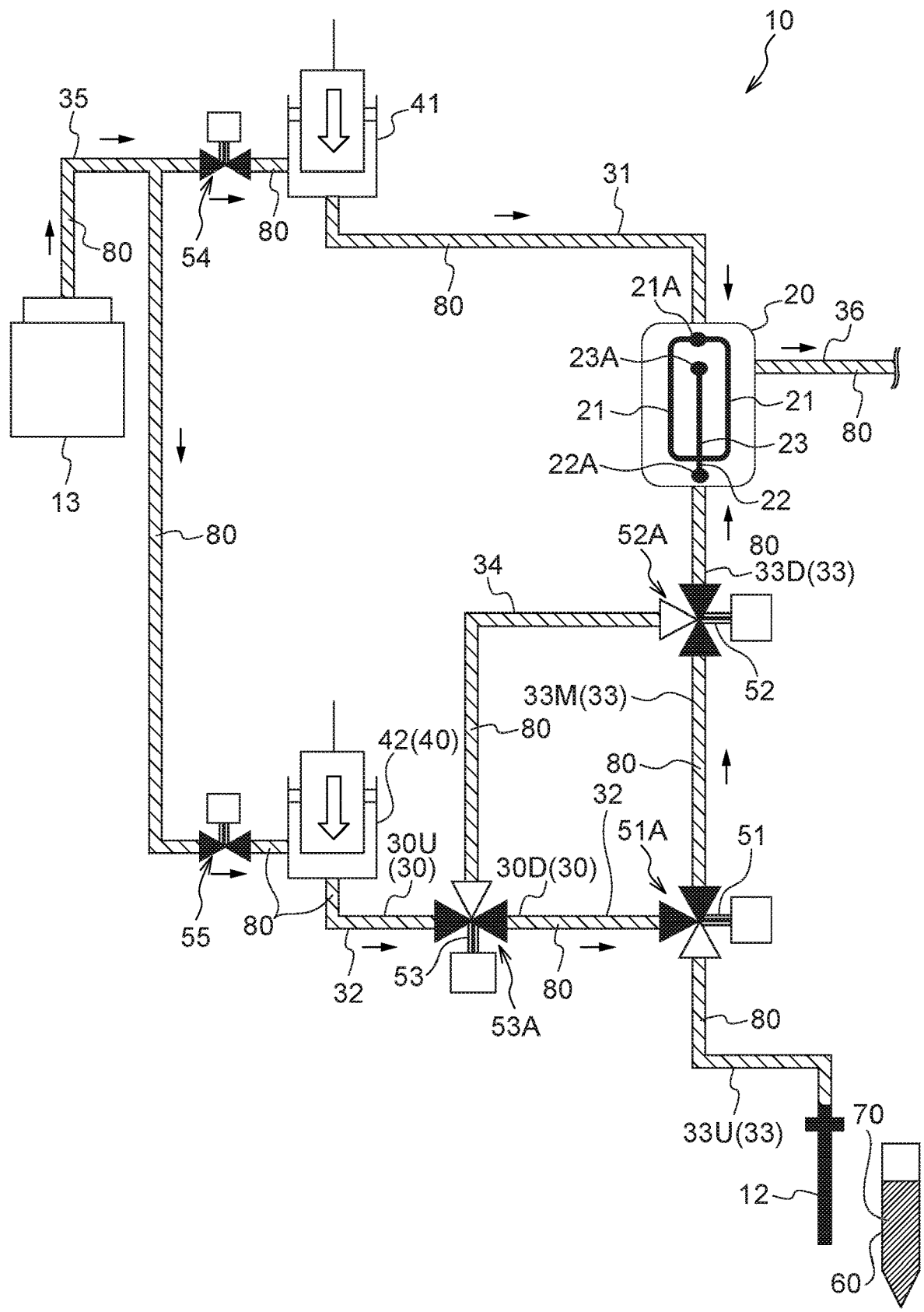

Next, as illustrated in FIG. 17, the first sheath fluid valve 54 is opened together with the second sheath fluid valve 55. Then the first switch controller 151 switches the flow paths of the first switch 51 so as to communicate the downstream section 30D of the sample extrusion path 32 with the midstream section 33M of the sample supply path 33, the second switch controller 152 switches the flow paths of the second switch 52 so as to communicate the midstream section 33M with the downstream section 33D of the sample supply path 33, and the third switch controller 153 switches the flow paths of the third switch 53 so as to communicate the upstream section 30U with the downstream section 30D of the specific flow path 30.

In this state the first pump controller 141 actuates the first pump 41, and the sheath fluid 80 is supplied to the sheath fluid supply path 31. Thereby, the sheath fluid 80 supplied from the sheath fluid storage unit 13 to the first pump 41 via the first sheath fluid valve 54 passes from the first pump 41 through the sheath fluid supply path 31, and reaches the sheath fluid port 21A of the flow cell 20. Namely, the sheath fluid supply path 31 from the first pump 41 to the sheath fluid port 21A of the flow cell 20 is all filled with the sheath fluid 80.

Simultaneously, the second pump controller 142 serving as the specific pump controller 140 actuates the second pump 42 serving as the specific pump 40, and the sheath fluid 80 is supplied to the sample extrusion path 32 serving as the specific flow path 30. Thereby, the sheath fluid 80 supplied from the sheath fluid storage unit 13 to the second pump 42 via the second sheath fluid valve 55 passes from the second pump 42 through the third switch 53, the first switch 51 and the second switch 52, and reaches the sample port 22A of the flow cell 20. Namely, the upstream section 30U of the sample extrusion path 32 from the second pump 42 to the third switch 53, the downstream section 30D of the sample extrusion path 32 from the third switch 53 to the first switch 51, the midstream section 33M of the sample supply path 33 from the first switch 51 to the second switch 52, and the downstream section 33D of the sample supply path 33 from the second switch 52 to the sample port 22A of the flow cell 20, are all filled with the sheath fluid 80.

Furthermore, in the flow cell 20, the sheath fluid 80 from the sheath fluid supply path 31 passes through the sheath fluid port 21A and fills the two branches of the sheath fluid flow path 21. On the other hand, the sheath fluid 80 from the sample extrusion path 32 passes through the sample port 22A and fills the sample flow path 22. Then, the sheath fluid 80 from both flow paths joins together in the confluent flow path 23, fills the confluent flow path 23, passes through the waste liquid port 23A, fills the waste liquid path 36, and is discharged to an external section, not illustrated in the drawings.

Thereby, the lines of the analysis device 10 are filled with the sheath fluid 80. Then, the first sheath fluid valve 54 and the second sheath fluid valve 55 are both closed. The first pump controller 141 and the second pump controller 142 then respectively halt actuation of the first pump 41 and the second pump 42.

Figure 18:
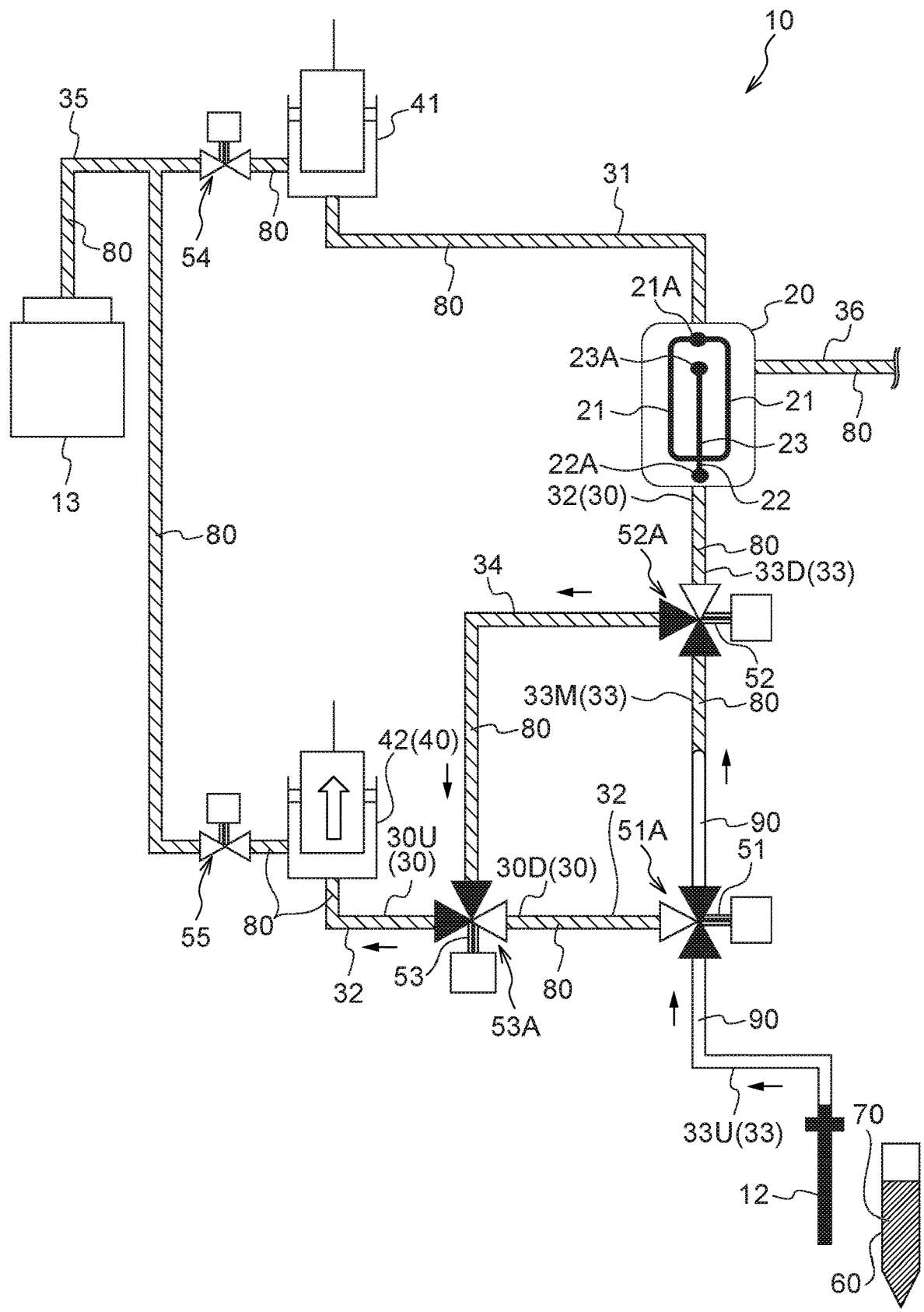

Then, at a flow path switching step S210 in FIG. 15A, as illustrated in FIG. 18, the first switch controller 151 switches the flow paths of the first switch 51 so as to communicate the upstream section 33U with the midstream section 33M of the sample supply path 33, the second switch controller 152 switches the flow paths of the second switch 52 so as to communicate the midstream section 33M of the sample supply path 33 with the branch flow path 34, and the third switch controller 153 switches the flow paths of the third switch 53 so as to communicate the branch flow path 34 with the upstream section 30U of the specific flow path 30.

In this state, at an air aspiration step S220 of FIG. 15A, the second pump controller 142 serving as the specific pump controller 140 actuates the second pump 42 serving as the specific pump 40 so as to impart negative pressure to the upstream section 30U of the sample extrusion path 32 serving as the specific flow path 30, and the sheath fluid 80 is aspirated from the upstream section 30U of the sample extrusion path 32 serving as the specific flow path 30. Thereby, the air 90 is aspirated from the aspirator 12. The aspirated air 90 flows from the upstream section 33U of the sample supply path 33 and reaches the midstream section 33M of the sample supply path 33 between the first switch 51 and the second switch 52.

Figure 19:
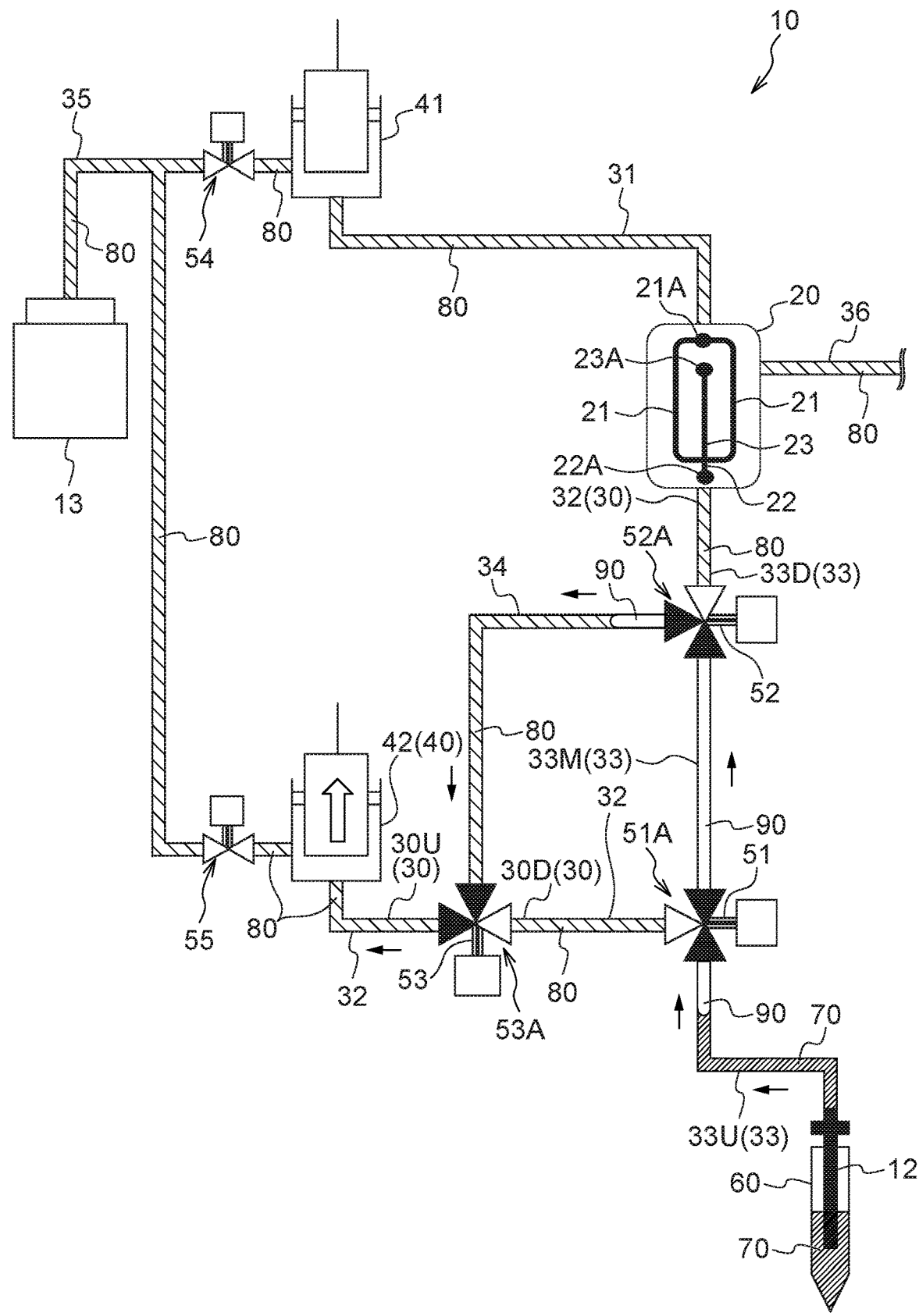

Then, at a sample aspiration step S230 of FIG. 15A, while maintaining the operation state of FIG. 18 and continuing to impart negative pressure to the upstream section 30U of the sample extrusion path 32 serving as the specific flow path 30, when the aspirator 12 is dipped in the liquid sample 70 contained in the sample container 60, as illustrated in FIG. 19, the liquid sample 70 is aspirated from the aspirator 12 into the upstream section 33U of the sample supply path 33. On the other hand, as illustrated in FIG. 19, the aspirated air 90 passes through the second switch 52 and reaches the branch flow path 34. The aspirated air 90 described above is interposed between the sheath fluid 80 filling the aspirator 12, and the liquid sample 70 aspirated by the aspirator 12, so that the sheath fluid 80 does not directly contact the liquid sample 70.

Figure 20:
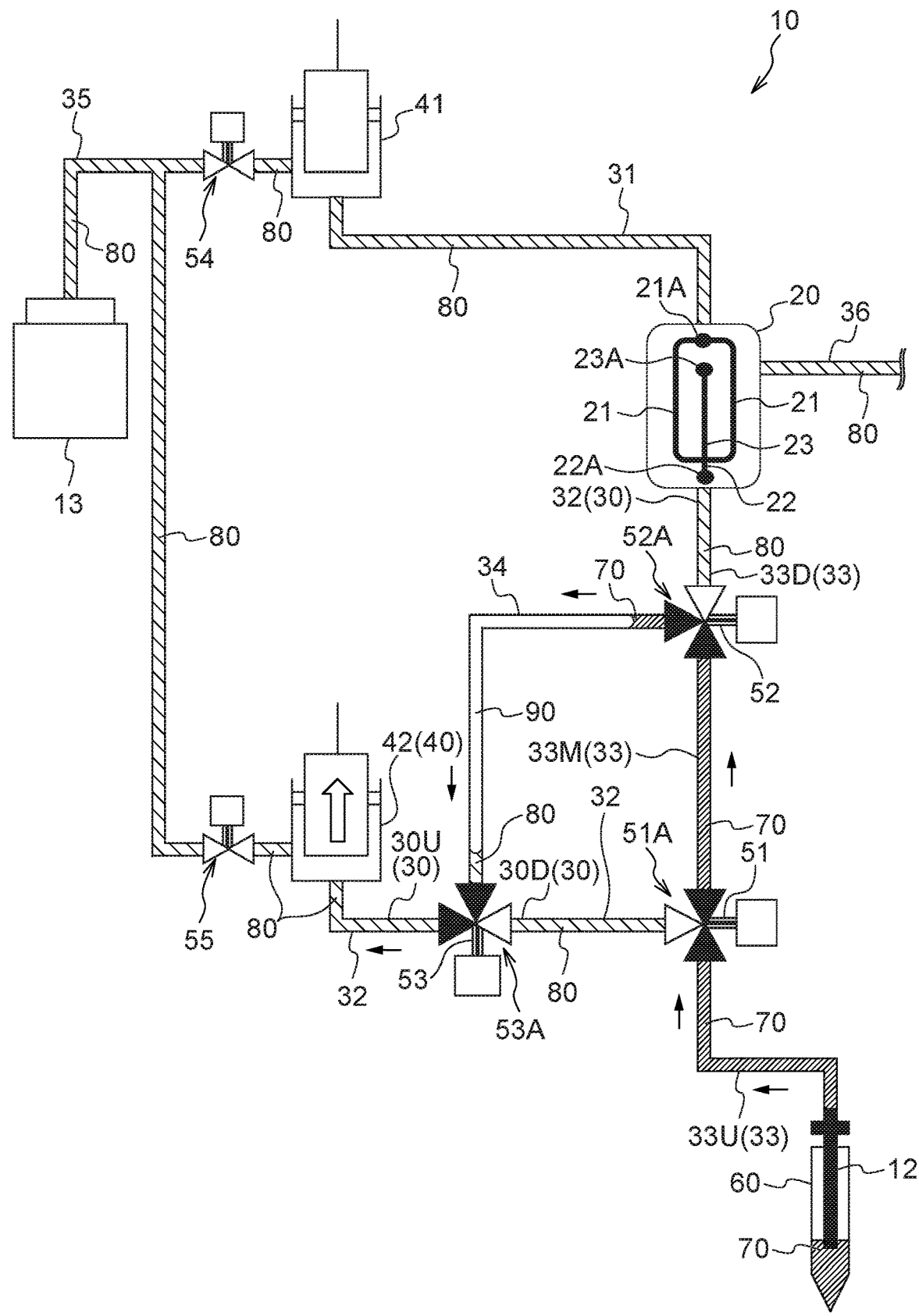

Next, as illustrated in FIG. 20, the entire amount of the aspirated air 90 passes the second switch 52 and reaches the branch flow path 34, the liquid sample 70 simultaneously aspirated reaches the midstream section 33M of the sample supply path 33, and a portion of the liquid sample 70 passes through the second switch 52 and reaches the branch flow path 34. Then, the second pump controller 142 serving as the specific pump controller 140 halts actuation of the second pump 42 serving as the specific pump 40, and stops imparting the negative pressure to the upstream section 30U of the sheath sample extrusion path 32 serving as the specific flow path 30. Thereby, the entire amount of the aspirated air 90 is accommodated inside the branch flow path 34.

Figure 21:
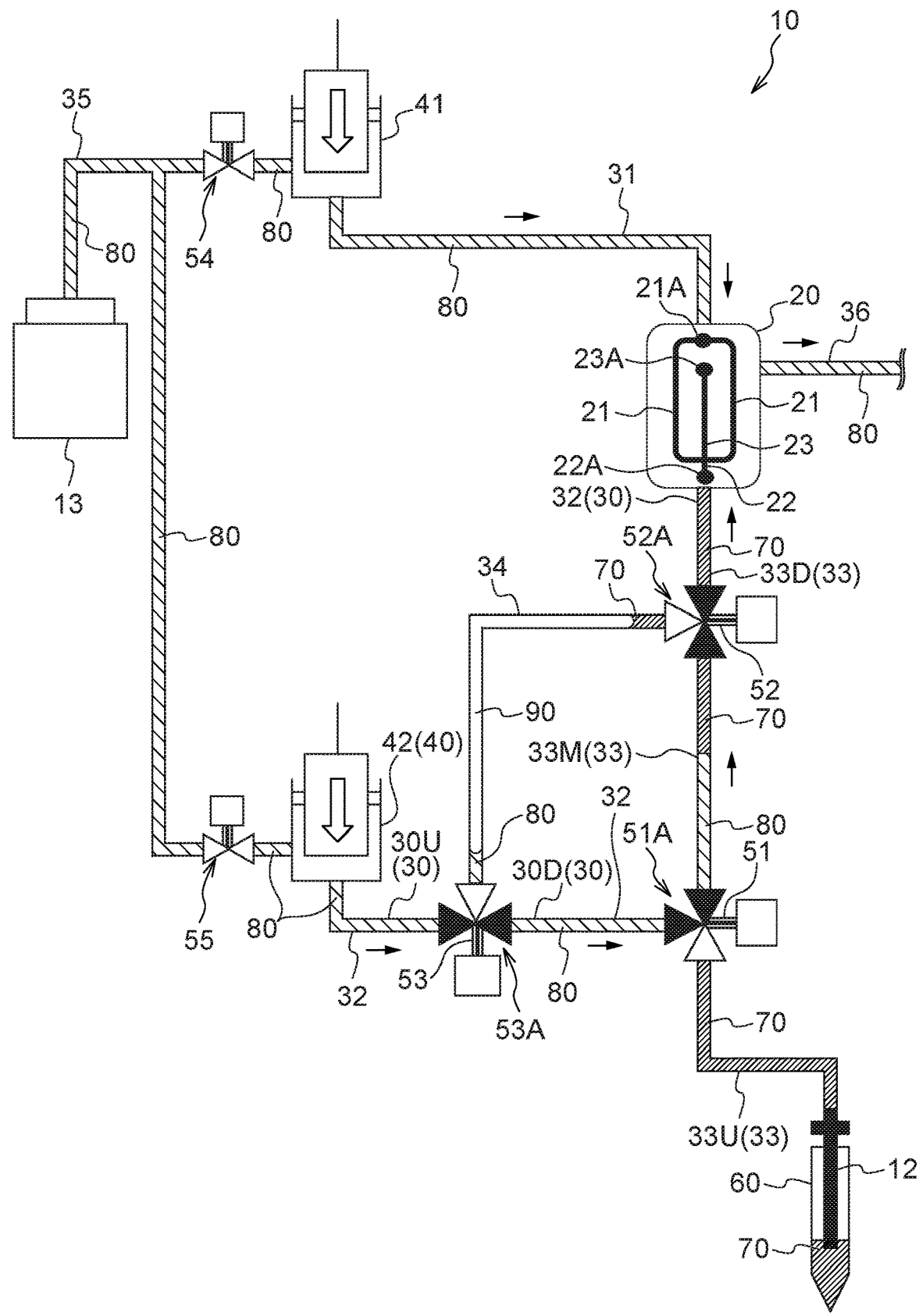

Then, at a flow path switching step S240 of FIG. 15B, as illustrated in FIG. 21, the first switch controller 151 switches the flow paths of the first switch 51 so as to communicate the sample extrusion path 32 with the midstream section 33M of the sample supply path 33, the second switch controller 152 switches the flow paths of the second switch 52 so as to communicate the midstream section 33M with the downstream section 33D of the sample supply path 33, and the third switch controller 153 switches the flow paths of the third switch 53 so as to communicate the upstream section 30U with the downstream section 30D of the specific flow path 30. Thereby, the entire amount of the aspirated air 90 is sealed inside the branch flow path 34.

In this state, at a sheath fluid/sample inflow step S250 of FIG. 15B, the first pump controller 141 actuates the first pump 41 so as to impart a positive pressure to the sheath fluid supply path 31, and the sheath fluid 80 is supplied again to the sheath fluid supply path 31. Thereby, the sheath fluid 80 flows through the sheath fluid supply path 31 from the first pump 41, and into the sheath fluid port 21A of the flow cell 20.

Simultaneously, the second pump controller 142 serving as the specific pump controller 140 actuates the second pump 42 serving as the specific pump 40 so as to impart a positive pressure to the sample extrusion path 32 serving as the specific flow path 30, and the sheath fluid 80 is supplied again to the sample extrusion path 32. Thereby, the sheath fluid 80, passing through the upstream section 30U of the specific flow path 30 from the second pump 42 to the third switch 53 and the downstream section 30D of the specific flow path 30 from the third switch 53 to the first switch 51, reaches the midstream section 33M of the sample supply path 33, extrudes the liquid sample 70 aspirated in this location, and causes the liquid sample 70 to flow from the second switch 52, through the downstream section 33D of the sample supply path 33, to the sample port 22A of the flow cell 20.

Figure 22:
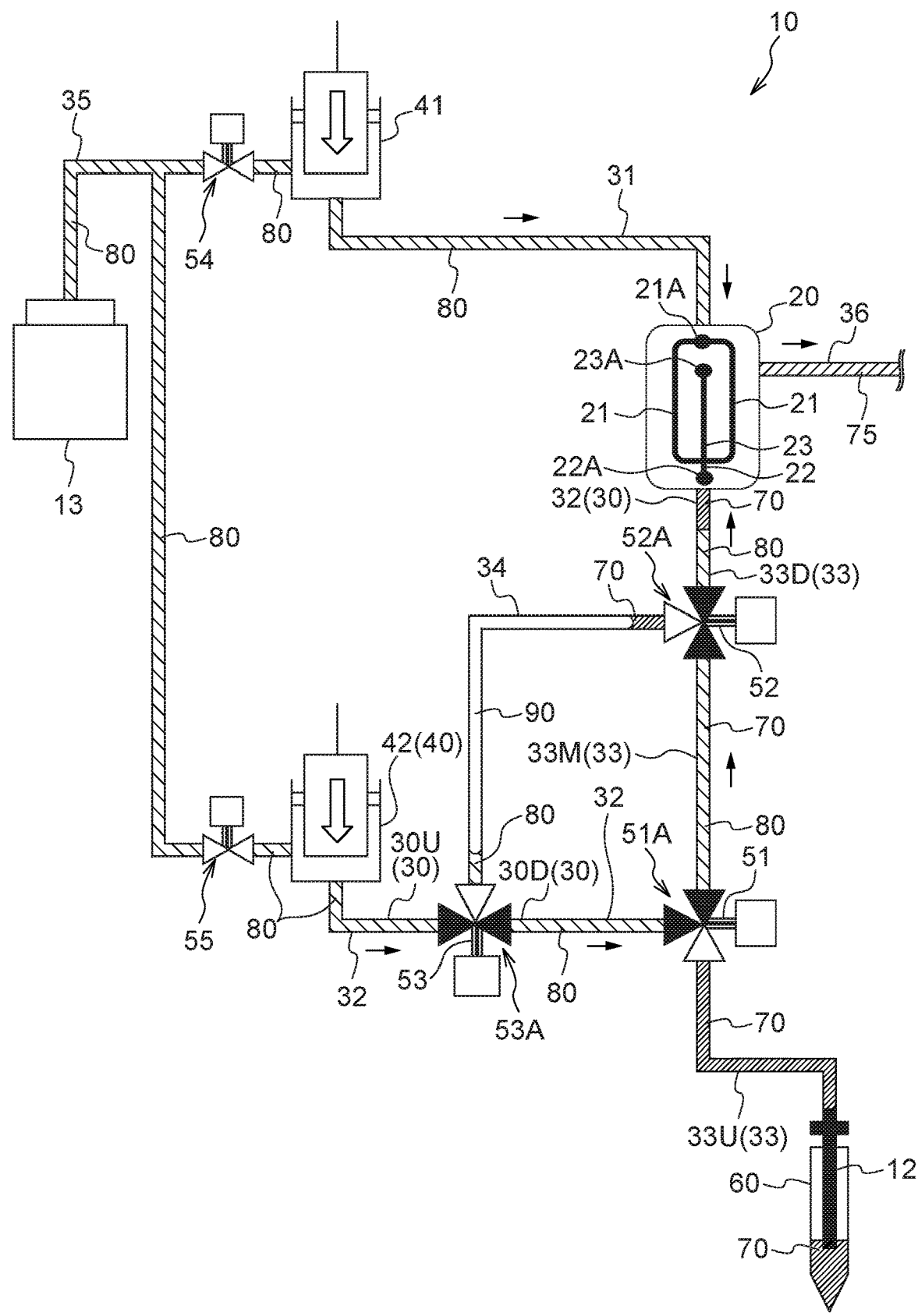

Then, at a sample measurement step S260 of FIG. 15B, as illustrated in FIG. 22, at the time when the sheath fluid 80 inflowing from the sample extrusion path 32, passing the second switch 52, reaches the downstream section 33D of the sample supply path 33, urine as the liquid sample 70 that flows from the sample port 22A of the flow cell 20 to the sample flow path 22 joins the sheath fluid 80 that flows from the two paths of the sheath fluid flow path 21, and reaches the confluent flow path 23. Measurement of urine as the liquid sample 70, by the measurement device 11 is similar to that in the first exemplary embodiment. Note that a waste liquid 75 that is a mixture of the liquid sample 70 and the sheath fluid 80 in the confluent flow path 23 is, at a waste liquid discharge step S270 of FIG. 15B, discharged from the waste liquid port 23A, through the waste liquid path 36, to an external section, not illustrated in the drawings, similarly to the first exemplary embodiment.

Note that pumps of the same capacity may be employed for the first pump 41 and the second pump 42, however, in cases in which pumps of different capacity are employed therefor, then it is preferable that the pump having the larger capacity is employed for the second pump 42 serving as the specific pump 40 to aspirate the sheath fluid 80 from the specific flow path 30.

Moreover, details relating to the volume of the branch flow path 34 are similar to those of the first exemplary embodiment.

INDUSTRIAL APPLICABILITY

The present disclosure is applicable to a liquid sample analysis method and to a liquid sample analysis device that employ a flow cell.

What is claimed is:

1. A liquid sample analysis method, employing:
a flow cell including a sheath fluid flow path, a sample flow path, a confluent flow path at which the sheath fluid flow path and the sample flow path join together, a sheath fluid port that is at an upstream end of the sheath fluid flow path, and a sample port that is at an upstream end of the sample flow path;
a sheath fluid supply path connected to the sheath fluid port;
an aspirator configured to aspirate a liquid sample and air;
a sample supply path that connects the aspirator and the sample port;
a sample extrusion path merging at a first branch point provided on the sample supply path;
a second branch point provided on the sample supply path between the first branch point and the sample port;
a third branch point provided either partway along the sheath fluid supply path or partway along the sample extrusion path;
a branch flow path interconnecting the second branch point and the third branch point; and
a first switch, a second switch, and a third switch respectively provided at the first branch point, the second branch point, and the third branch point, to enable switching of respective three flow paths located at each of the first branch point, the second branch point and the third branch point, the sample analysis method comprising:
switching flow paths of the first switch, the second switch and the third switch, so that a specific flow path, which is a flow path, among the sheath fluid supply path and the sample extrusion path, that is provided with the third branch point, communicates with the aspirator via the branch flow path;
aspirating air from the aspirator;
aspirating the liquid sample from the aspirator to the sample supply path so that an entire amount of the aspirated air is accommodated in the branch flow path;
switching the flow paths of the first switch, the second switch, and the third switch, so that the sample extrusion path communicates with the sample port, the sheath fluid supply path communicates with the sheath fluid port, and the branch flow path is isolated from both the sample supply path and the specific flow path;
causing a sheath fluid to flow from the sheath fluid supply path to the sheath fluid flow path and causing the sheath fluid to flow from the sample extrusion path to the sample supply path so that the liquid sample in the sample supply path is extruded and is caused to flow into the sample flow path; and
measuring, in the confluent flow path, the liquid sample from the sample flow path that is joined by the sheath fluid from the sheath fluid flow path.

2. The liquid sample analysis method of claim 1, wherein a volume of the entire amount of the air aspirated from the aspirator is smaller than a volume of the branch flow path.

3. The liquid sample analysis method of claim 2, wherein aspirating the liquid sample includes aspirating a portion of the liquid sample into the branch flow path.

4. The liquid sample analysis method of claim 3, wherein the liquid sample is a liquid specimen derived from a biological body.

5. The liquid sample analysis method of claim 4, wherein measuring the liquid sample includes acquiring an image of the liquid sample.

6. A liquid sample analysis device, comprising:
a flow cell including a sheath fluid flow path, a sample flow path, a confluent flow path at which the sheath fluid flow path and the sample flow path join together, a sheath fluid port that is at an upstream end of the sheath fluid flow path, and a sample port that is at an upstream end of the sample flow path;

a measurement device installed at a position facing toward the confluent flow path;

a sheath fluid supply path connected to the sheath fluid port;

a first pump provided on the sheath fluid supply path and configured to supply a sheath fluid to the sheath fluid supply path;

an aspirator configured to aspirate a liquid sample and air;

a sample supply path that connects the aspirator and the sample port;

a sample extrusion path joining a first branch point provided on the sample supply path;

a second pump provided on the sample extrusion path and configured to supply the sheath fluid to the sample extrusion path;

a sheath fluid storage unit configured to supply the sheath fluid to the first pump and the second pump;

a second branch point provided on the sample supply path between the first branch point and the sample port;

a third branch point provided either partway along the sheath fluid supply path or partway along the sample extrusion path;

a branch flow path interconnecting the second branch point and the third branch point;

a first switch, a second switch, and a third switch respectively provided at the first branch point, the second branch point, and the third branch point, to enable switching of respective three flow paths located at each of the first branch point, the second branch point and the third branch point; and a controller including a first pump controller configured to control the first pump, a second pump controller configured to control the second pump, a first switch controller configured to control flow path switching in the first switch, a second switch controller configured to control flow path switching in the second switch, a third switch controller configured to control flow path switching in the third switch, and a measurement controller configured to control measurement by the measurement device, wherein:

either the sheath fluid flow path or the sample extrusion path on which the third branch point is provided is referred to as a specific flow path;

either the first pump or the second pump that is provided on the specific flow path is referred to as a specific pump, which aspirates the liquid sample and air from the aspirator to the branch flow path;

either the first pump controller or the second pump controller that controls the specific pump is referred to as a specific pump controller;

a side closer to the flow cell in each of the specific flow path and the sample supply path is defined as a downstream side and an opposite side thereto is defined as an upstream side;

in a state in which the sheath fluid supply path, the sample supply path, the sample extrusion path and the branch flow path are filled with the sheath fluid, the first switch controller switches the first switch so that the flow paths at the first branch point communicate from the upstream side to the downstream side of the sample supply path, the second switch controller switches the second switch so that the flow paths at the second branch point communicate from the upstream side of the sample supply path to the branch flow path, and the third switch controller switches the third switch so that the flow paths at the third branch point communicate from the branch flow path to the upstream side of the specific flow path;

the specific pump controller actuates the specific pump to aspirate the air from the aspirator to the sample supply path, and further to aspirate the liquid sample from the aspirator to the sample supply path, and halts the actuation of the specific pump in a state in which an entire amount of the aspirated air passes the second branch point and is accommodated in the branch flow path;

the first switch controller switches the first switch so that the flow paths at the first branch point communicate from the sample extrusion path to the downstream side of the sample supply path, the second switch controller switches the second switch so that the flow paths at the second branch point communicate from the upstream side to the downstream side of the sample supply flow, and the third switch controller switches the third switch so that the flow paths at the third branch point communicate the upstream side with the downstream side of the specific flow path;

the first pump controller actuates the first pump to supply the sheath fluid into the sheath fluid supply path to cause the sheath fluid to flow into the sheath fluid flow path, and the second pump controller actuates the second pump to supply the sheath fluid into the sample extrusion path so as to extrude the liquid sample in the sample supply path to cause the liquid sample to flow into the sample flow path; and the measurement controller causes the measurement device to measure the liquid sample from the sample flow path in the confluent flow path.

7. The liquid sample analysis device of claim 6, wherein a volume of the entire amount of the air aspirated from the aspirator is smaller than a volume of the branch flow path.

8. The liquid sample analysis device of claim 7, wherein the specific pump controller actuates the specific pump and aspirates the sheath fluid from the specific flow path until a portion of the liquid sample reaches the branch flow path.

9. The liquid sample analysis device of claim 8, wherein the liquid sample is a liquid specimen derived from a biological body.

10. A fluid delivery method for delivering a liquid sample to a flow cell, the flow cell, a sample supply path, and an aspirator in this order being connected each other, the fluid delivery method comprising:

filling the aspirator, the sample supply path, and the flow cell, with a sheath fluid, aspirating air from the aspirator to the sample supply path, subsequently aspirating the liquid sample from the aspirator to the sample supply path, shunting the aspirated air to a branch flow path provided to the sample supply path by sending the liquid sample to the branch flow path, and sealing the branch path to prevent the air from flowing into the flow cell, and subsequently delivering the liquid sample to the flow cell.

* * * * *